(12) United States Patent
Dart et al.

(10) Patent No.: US 8,586,596 B2
(45) Date of Patent: Nov. 19, 2013

(54) COMPOUNDS AS CANNABINOID RECEPTOR LIGANDS

(75) Inventors: Michael J. Dart, Highland Park, IL (US); Teodozyj Kolasa, Lake Villa, IL (US)

(73) Assignee: AbbVie Inc., North Chicago, IL (US)

( * ) Notice: Subject to any disclaimer, the term of this patent is extended or adjusted under 35 U.S.C. 154(b) by 6 days.

(21) Appl. No.: 13/160,952

(22) Filed: Jun. 15, 2011

(65) Prior Publication Data

US 2011/0306616 A1    Dec. 15, 2011

Related U.S. Application Data

(60) Provisional application No. 61/354,922, filed on Jun. 15, 2010.

(51) Int. Cl.
    *A01N 43/90*      (2006.01)
    *A61K 31/519*     (2006.01)
    *C07D 487/00*     (2006.01)

(52) U.S. Cl.
    USPC ........................................ 514/265.1; 544/262

(58) Field of Classification Search
    USPC ........................................ 544/262; 514/265.1
    See application file for complete search history.

(56) References Cited

U.S. PATENT DOCUMENTS

| | | | |
|---|---|---|---|
| 7,511,013 B2 | 3/2009 | Molino et al. |
| 7,514,068 B2 | 4/2009 | Tung |
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 2008/0312435 A1 | 12/2008 | Saito et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0063022 A1 | 3/2010 | Carroll et al. |

FOREIGN PATENT DOCUMENTS

| | | |
|---|---|---|
| EP | 1820504 A1 | 8/2007 |
| WO | 9507271 A1 | 3/1995 |
| WO | 9710223 A1 | 3/1997 |
| WO | 2005099353 A2 | 10/2005 |
| WO | 2006008754 A1 | 1/2006 |
| WO | 2006051704 A1 | 5/2006 |
| WO | 2008063781 A2 | 5/2008 |
| WO | 2010033543 A2 | 3/2010 |

OTHER PUBLICATIONS

Arevalo-Martin, A., et al., "Therapeutic Action of Cannabinoids in a Murine Model of Multiple Sclerosis," Journal of Neuroscience, 2003, vol. 23 (7), pp. 2511-2516.
Benito C., et al., "Cannabinoid CB2 Receptors and Fatty Acid Amide Hydrolase are Selectively Overexpressed in Neuritic Plaque-Associated Glia in Alzheimer's Disease Brains," Journal of Neuroscience, 2003, vol. 23 (35), pp. 11136-11141.
Bennett G.J., et al., "A Peripheral Mononeuropathy in Rat that Produces Disorders of Pain Sensation like those Seen in Man," Pain, 1988, vol. 33 (1), pp. 87-107.
Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic, N. et al., "Role of heavy water in Boron Neutron Capture Therapy," Topics in Dosimetry & Treatment Planning for Neutron Capture Therapy, 1994, pp. 125-134.
Blake, M. I. et al., "Studies With Deuterated Drugs," Journal of Pharmaceutical Sciences, 1975, vol. 64 (3), pp. 367-391.
Bouchard J.F., et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle W.J., et al., "Osteoclast Differentiation and Activation," Nature, 2003, vol. 423 (6937), pp. 337-342.
Bozidar K., et al., "Transformations of 1,2,4-Thiadiazolo/2,3-X/ Azines," Heterocycles, 1987, vol. 26 (3), pp. 689-697.
Brennan T.J., et al., "Characterization of a Rat Model of Incisional Pain," Pain, 1996, vol. 64, pp. 493-501.
Brickner, S.J. et al., "Synthesis and Antibacterial Activity of U-100592 and U-100766, Two Oxazolidinone Antibacterial Agents for the Potential Treatment of Multidrug-Resistant Gram Positive Bacterial Infections," Journal of Medicinal Chemistry, 1996, vol. 39 (3), pp. 673-679.
Buckley N.E., et al., "Immunomodulation by Cannabinoids is Absent in Mice Deficient for the Cannabinoid CB2 Receptor, " European Journal of Pharmacology, 2000, vol. 396, pp. 141-149.
Carlisle S.J., et al., "Differential Expression of the CB2 Cannabinoid Receptor by Rodent Macrophages and Macrophage-like Cells in Relation to Cell Activation," International Immunopharmacology, 2002, vol. 2, pp. 69.
Carrier E.J., et al., "Endocannabinoids in Neuroimmunology and Stress," Current Drug Targets-CNS and Neurological Disorders, 2005, vol. 4, pp. 657-665.
CAS Registry No. 1061668-81-2, which entered STN on Oct. 15, 2008.

(Continued)

*Primary Examiner* — Paul V. Ward
(74) *Attorney, Agent, or Firm* — Lisa V. Mueller; Michael Best & Friedrich LLP

(57) ABSTRACT

Disclosed herein are cannabinoid receptor ligands of formula (I)

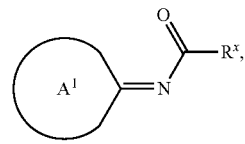

wherein $A^1$ and $R^x$ are as defined in the specification. Compositions comprising such compounds and methods for treating conditions and disorders using such compounds and compositions are also presented.

8 Claims, No Drawings

(56) References Cited

OTHER PUBLICATIONS

Casanova M.L., et al., "Inhibition of Skin Tumor Growth and Angiogenesis in vivo by Activation of Cannabinoid Receptors," Journal of Clinical Investigation, 2003, vol. 111 (1), pp. 43-50.

Chaplan S.R., et al., "Quantitative Assessment of Tactile Allodynia in the Rat Paw," Journal of Neuroscience Methods, 1994, vol. 53 (1), pp. 55-63.

Cichewicz D.L., "Synergistic Interactions Between Cannabinoid and Opioid Analgesics," Life Sciences, 2004, vol. 74 (11), pp. 1317-1324.

Clayton N., et al., "CB1 and CB2 Cannabinoid Receptors are Implicated in Inflammatory Pain," Pain, 2002, vol. 96 (3), pp. 253-260.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Czajka, D. M. et al., "Effect of Deuterium Oxide on the Reproductive Potential of Mice," Annals of the New York Academy of Sciences, 1960, vol. 84, pp. 770-779.

Czajka, D. M. et al., "Physiological Effects of Deuterium on Dogs," American Journal of Physiology, 1961, vol. 201 (2), pp. 357-362.

Dixon W.J., "Efficient Analysis of Experimental Observations," Annual Review of Pharmacology and Toxicology, 1980, vol. 20, pp. 441-462.

Filippo C.D., et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.

Foster, A. B. et al., "Deuterium Isotope Effects in the Metabolism of Drugs and Xenobiotics: Implications for Drug Design," Advances in Drug Research, 1985, vol. 14, pp. 2-36.

Galiégue S., et al., "Expression of Central and Peripheral Cannabinoid Receptors in Human Immune Tissues and Leukocyte Subpopulations," European Journal of Biochemistry, 1995, vol. 232 (1), pp. 54-61.

Goodman A.J., et al., "CB2 Selective Sulfamoyl Benzamides; Optimization of the Amide Functionality," Bioorganic & Medicinal Chemistry Letters, 2009, vol. 19 (2), pp. 309-313.

Greene T.W., et al., in: Protective Groups in Organic Synthesis, 3rd Edition, John Wiley and Sons, Inc., 1999, Preface, Table of Contents, Abbreviations.

Greene T.W., et al., "Protection for the Amino group," Protective Groups in Organic Synthesis, 1999, Third Edition, pp. 494-653.

Grotenhermen F., et al., "IACM 2nd Conference on Cannabinoids in Medicine," Expert Opinion in Pharmacotherapy, 2003, vol. 4 (12), pp. 2367-2371.

Hanus L., et al., "HU-308: A Specific Agonist for CB 2, a Peripheral Cannabinoid Receptor," Proceedings of the National Academy of Science, 1999, vol. 96, pp. 14228-14233.

Hohmann A.G., et al., "Selective Activation of Cannabinoid CB2 Receptors Suppresses Hyperalgesia Evoked by Intradermal Capsaicin," Journal of Pharmacology and Experimental Therapeutics, 2004, vol. 308, pp. 446-453.

Ibrahim M.M., et al., "Activation of CB2 Cannabinoid Receptors by AM1241 Inhibits Experimental Neuropathic Pain: Pain Inhibition by Receptors not Present in the CNS," Proceedings of the National Academy of Science, 2003, vol. 100 (18), pp. 10529-10533.

Ibrahim M.M., et al., "CB2 Cannabinoid Receptor Activation Produces Antinociception by Stimulating Peripheral Release of Endogenous Opioids," Proceedings of the National Academy of Science, 2005, vol. 102 (8), pp. 3093-3098.

Idris A.I., et al., "Regulation of Bone Mass, Bone Loss and Osteoclast Activity by Cannabinoid Receptors," Nature Medicine, 2005, vol. 11 (7), pp. 774-779.

Ihenetu K., et al., "Inhibition of Interleukin-8 Release in the Human Colonic Epithelial Cell Line HT-29 by Cannabinoids," European Journal of Pharmacology, 2003, vol. 458 (1-2), pp. 207-215.

International Search Report for Application No. PCT/US2010/028794, mailed Jul. 20, 2010, 3 pages.

International Search Report for Application No. PCT/US2010/028796, mailed Jul. 16, 2010, 4 pages.

International Search Report for Application No. PCT/US2011/040501, mailed on Oct. 24, 2011, 2 pages.

Jain S., et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.

Joshi S. K., et al., "Comparison of Antinociceptive Actoins of Standard Analgesics in Attenuating Capsaicin and Nerve-Injury-Induced Mechanical Hypersensitivty ," Neuroscience, 2006, vol. 143, pp. 587-596.

Julien B., et al., "Antifibrogenic Role of the Cannabinoid Receptor CB2 in the Liver," Gastroenterology, 2005, vol. 128, pp. 742-755.

Karsak M., et al., "Cannabinoid Receptor Type 2 Gene is Associated with Human Osteoporosis," Human Molecular Genetics, 2005, vol. 14 (22), pp. 3389-3396.

Kato, S. et al., "Synthesis of Deuterated Mosapride Citrate," Journal of Labelled Compounds and Radiopharmaceuticals, 1995, vol. 36 (10), pp. 927-932.

Kim S.H., et al., "An Experimental Model for Peripheral Neuropathy Produced by Segmental Spinal Nerve Ligation in the Rat," Pain, 1992, vol. 50 (3), pp. 355-363.

Koren B., et al., "Transformations of 1-(2-Chloropyridyl-3)-4-ethoxycarbonyl and 1-(2-Chloropyridy1-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.

Kushner, et al., "Pharmacological uses and perspectives of heavy water and deuterated compounds," Canadian Journal of Physiology and Pharmacology, 1999, vol. 77 (2), pp. 79-88.

Lepicier P., et al., "Endocannabinoids Protect the RAt Isolated Heart Against Ischaemia," British Journal of Pharmacology, 2003, vol. 139, pp. 805-815.

Lizondo, J. et al., "Linezolid: Oxazolidinone antibacterial," Drugs of the Future, 1996, vol. 21 (11), pp. 1116-1123.

Lotersztajn S., et al., "Hepatic Fibrosis: Molecular Mechanisms and Drug Targets," Annual Review of Pharmacology and Toxicology, 2005, vol. 45, pp. 605-628.

Malan T.P., et al., "CB2 Cannabinoid Receptor-Mediated Peripheral Antinociception," Pain, 2001, vol. 93, pp. 239-245.

Maligres, P.E., et al., "Stereocontrolled Preparation of a Nonpeptidal (-)-Spirobicyclic NK-1 Receptor Antagonist," Journal of Organic Chemistry, 2002, vol. 67 (4), pp. 1093-1101.

Mallesham, B. et al., "Highly Efficient Cul-Catalyzed Coupling Of Aryl Bromides With Oxazolidinones Using Buchwald's Protocol: A Short Route To Linezolid And Toloxatone," Organic Letters, 2003, vol. 5 (7), pp. 963-965.

Maresz K., et al., "Modulation of the Cannabinoid CB2 Receptor in Microglial Cells in Response to Inflammatory Stimuli," Journal of Neurochemistry, 2005, vol. 95, pp. 437-445.

Mathison R., et al., "Effects of Cannabinoid Receptor-2 Activation on Accelerated Gastrointestinal Transit in Lipopolysaccharide-Treated Rats," British Journal of Pharmacology, 2004, vol. 142, pp. 1247-1254.

McKallip R.J., et al., "Targeting CB2 Cannabinoid Receptors as a Novel Therapy to Treat Malignant Lymphoblastic Disease," Blood, 2002, vol. 15 (2), pp. 627-634.

Miyaura N., et al., ed., Topics in Current Chemistry: Cross-Coupling Reactions, Springer, 2002, Table of Contents.

Nackley A.G., et al., "Selective Activation of Cannabinoid CB2 Receptors Suppresses Spinal fos Protein Expression and Pain Behavior in a Rat Model of Inflammation," Neuroscience, 2003, vol. 119, pp. 747-757.

Negishi E., et al., eds., Handbook of Organopalladium Chemistry for Organic Synthesis, vol. 1, John Wiley & Sons, 2002, Table of Contents.

Ni X., et al., "Win 55212-2, a Cannabinoid Receptor Agonist, Attenuates Leukocyte/Endothelial Interactions in an Experimental Autoimmune Encephalomyelitis Model," Multiple Sclerosis, 2004, vol. 10, pp. 158-164.

Non-Final Office Action mailed Mar. 9, 2012 for U.S. Appl. No. 12/732,428, filed Mar. 26, 2010.

(56) References Cited

OTHER PUBLICATIONS

Patel H.J., et al., "Inhibition of Guinea-Pig and Human Sensory Nerve Activity and the Cough Reflex in Guinea-Pigs by Cannabinoid (CB2) Receptor Activation," British Journal of Pharmacology, 2003, vol. 140 (2), pp. 261-268.

Pertwee R.G., "Cannabinoids and Multiple Sclerosis," Pharmacology & Therapeutics, 2002, vol. 95, pp. 165-174.

Poste G. et al., "Lipid Vesicles as Carriers for Introducing Biologically Active Materials into Cells," Methods in Cell Biology, 1976, vol. 14, pp. 33-71.

Quartilho A., et al., "Inhibition of Inflammatory Hyperalgesia by Activation of Peripheral CB2 Cannabinoid Receptors," Anesthesiology, 2003, vol. 99, pp. 955-960.

Radulescu C., et al., "Actes Du Colloque Franco-Roumain De Chimie Appliquee, 3Rd, Bacau, Romania," 2004, pp. 117-120.

Radulescu C., et al., "The Comparative Study on the Synthesis Methods of a Heterocyclic System 2-Aminothiazolo[4,5-13]Pyricline, " Revista de Chimie, 2005, vol. 56 (6) pp. 659-662.

Radulescu C., et al., "Synthesis and Characteristics of Compact Condensed Heterocyclic System 2-Aminothiazolo[5,4-c]Pyridine, " Revista de Chimie, 2004, vol. 55 (11), pp. 889-893.

Ramirez B.G., et al., "Prevention of Alzheimers Disease Pathology by Cannabinoids: Neuroprotection Mediated by Blockade of Microglial Activation," Journal of Neuroscience, 2005, vol. 25 (8), pp. 1904-1913.

Sanchez C., et al., "Inhibition of Glioma Growth in Vivo by Selective Activation of the CB2 Cannabinoid Receptor1," Cancer Research, 2001, vol. 61, pp. 5784-5789.

Steffens S., et al., "Low Dose Oral Cannabinoid Therapy Reduces Progression of Atherosclerosis in Mice," Nature, 2005, vol. 434, pp. 782-786.

Thomson, J.F., "Physiological Effects Of D20 In Mammals," Annals of the New York Academy of Sciences, 1960, vol. 84, pp. 736-744.

Valenzano K.J., et al., "Pharmacological and Pharmacokinetic Characterization of the Cannabinoid Receptor 2 Agonist, Gw405833, Utilizing Rodent Models of Acute and Chronic Pain, Anxiety, Ataxia and Catalepsy," Neuropharmacology, 2005, vol. 48, pp. 658-672.

Warhurst A.C., et al., "Interferon Gamma Induces Differential Upregulation of Alpha and Beta Chemokine Secretion in Colonic Epithelial Cell Lines," Gut, 1998, vol. 42 (2), pp. 208-213.

Wright K., et al., "Differential Expression of Cannabinoid Receptors in the Human Colon: Cannabinoids Promote Epithelial Wound Healing ," Gastroenterology, 2005, vol. 129 (2), pp. 437-453.

Yoshihara S., et al., "Cannabinoid Receptor Agonists Inhibit Sensory Nerve Activation in Guinea Pig Airways," American Journal of Respiratory and Critical Care Medicine, 2004, vol. 170 (9), pp. 941-946.

Yoshihara S., et al., "Endogenous Cannabinoid Receptor Agonists Inhibit Neurogenic Inflammations in Guinea Pig Airways," Allergy and Immunology, 2005, vol. 138, pp. 80-87.

Yoshihara S., et al., "The Cannabinoid Receptor Agonist WIN 55212-2 Inhibits Neurogenic Inflammations in Airway Tissues ," Journal of Pharmacological Sciences, 2005, vol. 98 (1), pp. 77-82.

COMPOUNDS AS CANNABINOID RECEPTOR LIGANDS

This application claims priority to U.S. Patent Application Ser. No. 61/354,922, filed on Jun. 15, 2010, and is incorporated herein by reference.

TECHNICAL FIELD

Compounds that are cannabinoid receptor ligands, compositions comprising such compounds, and methods for treating conditions and disorders using such compounds and compositions, are disclosed herein.

BACKGROUND OF THE INVENTION (−)-$\Delta^9$-Tetrahydrocannabinol ($\Delta^9$-THC), the major psychoactive constituent of marijuana, exerts a broad range of effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in pre-clinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-operative pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, fibromyalgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds presented herein are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY OF THE INVENTION

Disclosed herein are compounds of formula (I)

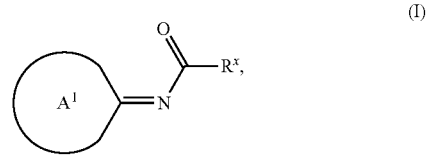

(I)

or pharmaceutically acceptable salts, solvates, or salts of solvates thereof, wherein $R^x$ is aryl, cycloalkyl, cycloalkenyl, heteroaryl, or heterocycle, each of which is independently unsubstituted or substituted with 1, 2, 3, or 4 substituents independently selected from the group consisting of alkyl, alkenyl, alkynyl, halogen, haloalkyl, oxo, $G^a$, —CN, $NO_2$, —$OR^a$, —OC(O)$R^e$, —OC(O)N($R^f$)$_2$, —OS(O)$_2R^e$, —S(O)$_2R^e$, —S(O)$_2$N($R^f$)$_2$, —C(O)$R^f$, —C(O)O$R^f$, —C(O)N($R^f$)$_2$, —N($R^f$)$_2$, —N($R^f$)C(O)$R^e$, —N($R^f$)S(O)$_2R^e$, —N($R^f$)C(O)O($R^e$), —N($R^f$)C(O)N($R^f$)$_2$, —(C$R^{1a}R^{1b}$)$_{q1}$-$G^a$, —(C$R^{1a}R^{1b}$)$_{q1}$—$OR^a$, —(C$R^{1a}R^{1b}$)$_{q1}$—OC(O)$R^e$, —(C$R^{1a}R^{1b}$)$_{q1}$—OC(O)N($R^f$)$_2$, —(C$R^{1a}R^{1b}$)$_{q1}$—OS(O)$_2R^e$, —(C$R^{1a}R^{1b}$)$_{q1}$—S(O)$_2R^e$, —(C$R^{1a}R^{1b}$)$_{q1}$—S(O)$_2$N($R^f$)$_2$, —(C$R^{1a}R^{1b}$)$_{q1}$—C(O)$R^f$, —(C$R^{1a}R^{1b}$)$_{q1}$—C(O)O$R^f$, —(C$R^{1a}R^{1b}$)$_{q1}$—C(O)N($R^f$)$_2$, —(C$R^{1a}R^{1b}$)$_{q1}$—N($R^f$)$_2$, —(C$R^{1a}R^{1b}$)$_{q1}$—N($R^f$)C(O)$R^e$, —(C$R^{1a}R^{1b}$)$_{q1}$—N(R)S(O)$_2R^e$, —(C$R^{1a}R^{1b}$)$_{q1}$—N($R^f$)C(O)O($R^e$), —(C$R^{1a}R^{1b}$)$_{q1}$—N($R^f$)C(O)N($R^f$)$_2$, and —(C$R^{1a}R^{1b}$)$_{q1}$—CN;

$R^a$ is $G^a$, —(C$R^{1c}R^{1d}$)$_{q2}$-$G^a$, —(C$R^{1c}R^{1d}$)$_{q2}$—C(O)$R^b$, —(C$R^{1c}R^{1d}$)$_{q2}$—S(O)$_2R^e$, —(C$R^{1c}R^{1d}$)$_{q2}$—C(O)N($R^d$)$_2$, —(C$R^{1c}R^{1d}$)$_{q2}$—C(S)N($R^d$)$_2$, —(C$R^{1c}R^{1d}$)$_{q2}$—SO$_2$N($R^d$)$_2$, —(C$R^{1c}R^{1d}$)$_{q2}$—C(=NO$R^b$)$R^b$, —(C$R^{1c}R^{1d}$)$_{q2}$—CN, —(C$R^{1c}R^{1d}$)$_{q2}$—N($R^d$)C(O)$R^e$, —(C$R^{1c}R^{1d}$)$_{q2}$—N($R^d$)C(O)O$R^e$, —(C$R^{1c}R^{1d}$)$_{q2}$—N($R^d$)S(O)$_2R^e$, —(C$R^{1c}R^{1d}$)$_{q2}$—N($R^d$)C(O)N($R^d$)$_2$, —(C$R^{1c}R^{1d}$)$_{q2}$—N($R^d$)S(O)$_2$N($R^d$)$_2$, —(C$R^{1c}R^{1d}$)$_{q4}$—N($R^d$)$_2$, —(C$R^{1c}R^{1d}$)$_{q4}$—$OR^b$, —(C$R^{1c}R^{1d}$)$_{q2}$—OC(O)$R^b$, N($R^d$)C(O)$R^e$, N($R^d$)C(O)O$R^e$, N($R^d$)C(O)N($R^d$)$_2$, N($R^d$)$_2$, or N=C($R^p$)($R^q$);

$R^p$ is hydrogen, alkyl, haloalkyl, —(C$R^{1c}R^{1d}$)$_{q2}A^2$, —C(O)O$R^b$, —C(O)$R^b$, $G^{1d}$, or —(C$R^{1c}R^{1d}$)$_{q2}$-$G^{1d}$;

$R^q$ is hydrogen, alkyl, haloalkyl, N($R^d$)$_2$, —(C$R^{1c}R^{1d}$)$_{q2}$-$A^2$, $G^{1d}$, or —(C$R^{1c}R^{1d}$)$_{q2}$-$G^{1d}$; or $R^p$ and $R^q$, together with the carbon atom to which they are attached, form a monocyclic or bicyclic ring selected from the group consisting of cycloalkyl and heterocycle, each of which is optionally substituted with 1, 2, 3, 4, or 5 substituents independently selected from the group consisting of oxo, alkyl, haloalkyl, and halogen;

$G^{1d}$, at each occurrence, is independently a monocyclic heterocycle, a monocyclic heteroaryl, a phenyl, a monocyclic cycloalkyl, or a monocyclic cycloalkenyl; each of which is optionally substituted with 1, 2, 3, or 4 substituents independently selected from the group consisting of —N(R)$_2$, —CN, oxo, alkyl, haloalkyl, alkoxy, haloalkoxy, halogen, and hydroxy;

$A^2$, at each occurrence, is independently C(O)R$^b$, —S(O)$_2$R$^c$, —C(O)N(R$^d$)$_2$, —C(S)N(R$^d$)$_2$, —S(O)$_2$N(R$^d$)$_2$, —C(=NOR$^b$)R$^b$, —N(R$^d$)C(O)R$^b$, —N(R$^d$)C(O)OR$^c$, —N(R$^d$)S(O)$_2$R$^c$, —N(R$^d$)C(O)N(R$^d$)$_2$, —N(R$^d$)S(O)$_2$N(R$^d$)$_2$, —CN, —OR$^b$, or —N(R$^d$)$_2$;

$G^a$ at each occurrence, is independently aryl, heteroaryl, cycloalkyl, cycloalkenyl, or heterocycle, each of which is independently unsubstituted or substituted with 1, 2, 3, or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, G$^b$, oxo, —CN, NO$_2$, —OR$^g$, —OC(O)R$^g$, —OC(O)N(R$^g$)$_2$, —S(O)$_2$R$^h$, —S(O)$_2$N(R$^g$)$_2$, —C(O)R$^g$, —C(O)OR$^g$, —C(O)N(R$^g$)$_2$, —N(R$^g$)$_2$, —N(R$^g$)C(O)R$^g$, —N(R$^f$)S(O)$_2$R$^h$, —N(R$^g$)C(O)O(R$^g$), —N(R$^g$)C(O)N(R$^g$)$_2$, —(CR$^{1e}$R$^{1f}$)$_{q3}$-G$^b$, —(CR$^{1e}$R$^{1f}$)$_{q3}$—OR$^g$, —(CR$^{1e}$R$^{1f}$)$_{q3}$—OC(O)R$^g$, —(CR$^{1e}$R$^{1f}$)$_{q3}$—OC(O)N(R$^g$)$_2$, —(CR$^{1e}$R$^{1f}$)$_{q3}$—S(O)$_2$R$^h$, —(CR$^{1e}$R$^{1f}$)$_{q3}$—S(O)$_2$N(R$^g$)$_2$, —(CR$^{1e}$R$^{1f}$)$_{q3}$—C(O)R$^g$, —(CR$^{1e}$R$^{1f}$)$_{q3}$—C(O)OR$^g$, —(CR$^{1e}$R$^{1f}$)$_{q3}$—C(O)N(R$^g$)$_2$, —(CR$^{1e}$R$^{1f}$)$_{q3}$—N(R$^g$)$_2$, —(CR$^{1e}$R$^{1f}$)$_{q3}$—N(R$^g$)C(O)R$^g$, —(CR$^{1e}$R$^{1f}$)$_{q3}$—N(R$^g$)S(O)$_2$R$^h$, —(CR$^{1e}$R$^{1f}$)$_{q3}$—N(R$^g$)C(O)O(R$^g$), —(CR$^{1e}$R$^{1f}$)$_{q3}$—N(R$^g$)C(O)N(R$^g$)$_2$, and —(CR$^{1e}$R$^{1f}$)$_{q3}$—CN;

$G^b$, at each occurrence, is independently aryl, heteroaryl, cycloalkyl, cycloalkenyl, or heterocycle, each of which is independently unsubstituted or substituted with 1, 2, 3, or 4 substituents selected from the group consisting of C$_1$-C$_4$ alkyl, C$_2$-C$_4$ alkenyl, C$_2$-C$_4$ alkynyl, halogen, C$_1$-C$_4$ haloalkyl, —CN, NO$_2$, —OR$^j$, —OC(O)R$^j$, —OC(O)N(R$^j$)$_2$, —S(O)$_2$R$^k$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^j$, —N(R$^j$)S(O)$_2$R$^j$, —N(R$^j$)C(O)O(R$^j$), —N(R$^j$)C(O)N(R$^j$)$_2$, —(CR$^{1e}$R$^{1f}$)$_{q3}$—OR$^j$, —(CR$^{1e}$R$^{1f}$)$_{q3}$—OC(O)R$^j$, —(CR$^{1e}$R$^{1f}$)$_{q3}$—OC(O)N(R$^j$)$_2$, —(CR$^{1e}$R$^{1f}$)$_{q3}$—S(O)$_2$R$^k$, —(CR$^{1e}$R$^{1f}$)$_{q3}$—S(O)$_2$N(R$^j$)$_2$, —(CR$^{1e}$R$^{1f}$)$_{q3}$—C(O)R$^j$, —(CR$^{1e}$R$^{1f}$)$_{q3}$—C(O)OR$^j$, —(CR$^{1e}$R$^{1f}$)$_{q3}$—C(O)N(R$^j$)$_2$, —(CR$^{1e}$R$^{1f}$)$_{q3}$—N(R$^j$)$_2$, —(CR$^{1e}$R$^{1f}$)$_{q3}$—N(R$^j$)C(O)R$^j$, —(CR$^{1e}$R$^{1f}$)$_{q3}$—N(R$^j$)S(O)$_2$R$^k$, —(CR$^{1e}$R$^{1f}$)$_{q3}$—N(R$^j$)C(O)O(R$^j$), —(CR$^{1e}$R$^{1f}$)$_{q3}$—N(R$^j$)C(O)N(R$^j$)$_2$, and —(CR$^{1e}$R$^{1f}$)$_{q3}$—CN;

R$^b$, R$^d$, and R$^f$, at each occurrence, are each independently hydrogen, alkyl, haloalkyl, G$^b$, hydroxyalkyl, alkoxyalkyl, haloalkoxyalkyl, or —(C$_1$-C$_6$ alkylene)-G$^a$;

R$^c$ and R$^e$, at each occurrence, are each independently alkyl, haloalkyl, G$^a$, hydroxyalkyl, alkoxyalkyl, haloalkoxyalkyl, or —(C$_1$-C$_6$ alkylene)-G$^a$;

R$^{1a}$, R$^{1b}$, R$^{1c}$, R$^{1d}$, R$^{1e}$, and R$^{1f}$, at each occurrence, are each independently hydrogen, halogen, alkyl, or haloalkyl;

R$^g$, at each occurrence, is independently hydrogen, alkyl, haloalkyl, G$^b$, hydroxyalkyl, alkoxyalkyl, haloalkoxyl, or —(C$_1$-C$_6$ alkylene)-G$^b$;

R$^h$, at each occurrence, is independently alkyl, haloalkyl, G$^b$, hydroxyalkyl, alkoxyalkyl, haloalkoxy, or —(C$_1$-C$_6$ alkylene)-G$^b$;

R$^j$, at each occurrence, is independently hydrogen, alkyl, or haloalkyl;

R$^k$, at each occurrence, is independently alkyl or haloalkyl;

A$^1$ is formula (a), (b), or (c):

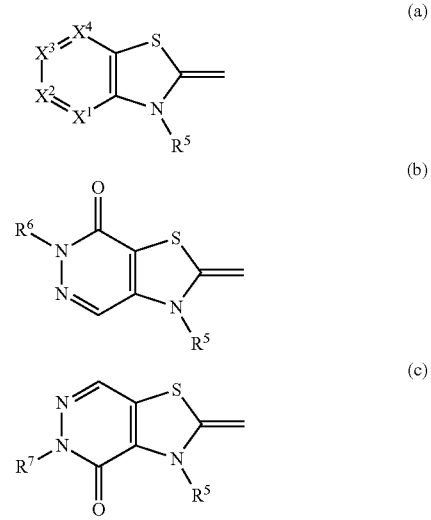

X$^1$ is CR$^1$ or N;
X$^2$ is CR$^2$ or N;
X$^3$ is CR$^3$ or N;
X$^4$ is CR$^4$ or N;
with the proviso that two of X$^1$, X$^2$, X$^3$, and X$^4$ are N;

R$^1$, R$^2$, R$^3$, and R$^4$, can be the same or different, are each independently hydrogen, hydroxy, alkoxy, haloalkoxy, halogen, alkyl, or haloalkyl;

R$^5$, at each occurrence, is the same or different, and is independently C$_2$-C$_{10}$ alkyl, alkenyl, alkynyl, haloalkyl, —(CR$^{5a}$R$^{5b}$)$_{q4}$—O-haloalkyl, —(CR$^{5a}$R$^{5b}$)$_{q4}$—O-G$^{5a}$, —(CR$^{5a}$R$^{5b}$)$_{q4}$—O—(CR$^{5e}$R$^{5d}$)$_{q5}$-G$^{5a}$, —(CR$^{5a}$R$^{5b}$)$_{q5}$—C(O)—R$^g$, —(CR$^{5a}$R$^{5b}$)$_{q5}$—C(=N—OR$^g$)R$^g$, —(CR$^{5a}$R$^{5b}$)$_{q5}$—SO$_2$—R$^h$, —(CR$^{5a}$R$^{5b}$)$_{q5}$-G$^{5b}$, —(CR$^{5a}$R$^{5b}$)$_{q5}$—C(O)N(R$^g$)$_2$, —(CR$^{5a}$R$^{5b}$)$_{q4}$—OC(O)N(R$^g$)$_2$, or —(CR$^{5a}$R$^{5b}$)$_{q5}$—CN;

R$^{5a}$, R$^{5b}$, R$^{5c}$, and R$^{5d}$, at each occurrence, are each independently hydrogen or alkyl;

q1, q2, q3, and q5, at each occurrence, are each independently 1, 2, 3, 4, or 5;

q4, at each occurrence, is independently 2, 3, 4, or 5;

G$^{5a}$, at each occurrence, is independently cycloalkyl, cycloalkenyl, heterocycle, aryl, or heteroaryl;

G$^{5b}$ is cycloalkyl, cycloalkenyl, thien-2-yl, or thien-3-yl;

wherein the rings as represented by G$^{5a}$ and G$^{5b}$ are each optionally substituted with 1, 2, 3, 4, or 5 substituents independently selected from the group consisting of oxo, alkyl, halogen, hydroxy, alkoxy, haloalkoxy, and haloalkyl; and R$^6$ and R$^7$, are the same or different, and are each independently C$_1$-C$_6$ alkyl, haloalkyl, hydroxyalkyl, or alkoxyalkyl.

Another aspect relates to pharmaceutical compositions comprising therapeutically effective amount of a compound described herein or pharmaceutically acceptable salt, solvate, or salt of solvate thereof, in combination with a pharmaceutically acceptable carrier. Such compositions can be administered in accordance with methods described herein, typically as part of a therapeutic regimen for treatment or prevention of conditions and disorders related to cannabinoid (CB) receptor subtype CB$_2$. More particularly, the methods are useful for treating conditions related to pain such as, but not limited to, chronic pain, neuropathic pain, nociceptive pain, osteoarthritic pain, inflammatory pain, cancer pain, fibromyalgia, post herpetic neuralgia, lower back pain, post operative pain, and eye pain; inflammatory disorders, immune disorders, neurological disorders, cancers of the immune system, respiratory disorders, obesity, diabetes, cardiovascular disorders, or for providing neuroprotection.

Further, provided herein are uses of the present compounds or pharmaceutically acceptable salts, solvates, or salts of solvates thereof, in the manufacture of medicaments for the treatment of the disease or conditions described above, alone or in combination with a pharmaceutically acceptable carrier, particularly for the treatment of pain such as, but not limited to, chronic pain, neuropathic pain, nociceptive pain, osteoarthritic pain, inflammatory pain, cancer pain, fibromyalgia, post herpetic neuralgia, lower back pain, post operative pain, and eye pain, or combinations thereof.

The compounds, compositions comprising the compounds, pharmaceutically acceptable salts, solvates, or salts of the solvates thereof, and methods for treating or preventing conditions and disorders by administering the compounds or compositions thereof, are further described herein.

These and other objectives are described further in the following paragraphs. These objectives should not be deemed to narrow the scope of the invention.

DETAILED DESCRIPTION OF THE INVENTION

Compounds of formula (I)

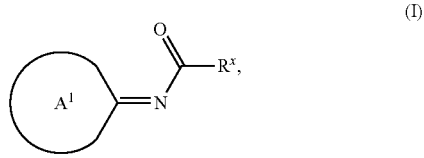

wherein $A^1$ and $R^x$ are as defined above in the Summary and below in the Detailed Description are disclosed. Compositions comprising such compounds and methods for treating conditions and disorders using such compounds and compositions are also disclosed.

In various embodiments, compounds described herein can contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. DEFINITIONS

It is noted that, as used in this specification and the intended claims, the singular form "a," "an," and "the" includes plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. The term "$C_1$-$C_4$ alkoxy" as used herein, means a $C_1$-$C_4$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Non-limiting examples of alkoxyalkyl include tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. For example "$C_1$-$C_4$ alkyl" means a straight or branched chain, saturated hydrocarbon containing 1 to 4 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain of 1 to 10 carbon atoms, for example, of 1 to 4 carbon atoms. Examples of alkylene and alkylenyl include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group containing from 2 to 4 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryl groups can be unsubstituted or substituted, and the bicyclic aryl is attached to the parent molecular moiety through any substitutable carbon atom contained within the bicyclic ring system.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. Tricyclic cycloalkyls are exemplified by a bicyclic cycloalkyl fused to a monocyclic cycloalkyl. The monocyclic or bicyclic cycloalkyl ring can contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkoxy" as used herein, means an alkoxy group, as defined herein, in which one, two, three, four, five or six hydrogen atoms are replaced by halogen. The term "$C_1$-$C_4$ haloalkoxy" as used herein, means a $C_1$-$C_4$ alkoxy group, as defined herein, in which one, two, three, four, five or six hydrogen atoms are replaced by halogen. Non-limiting examples of haloalkoxy include 2-fluoroethoxy, 2,2,2-trifluoroethoxy, trifluoromethoxy, and difluoromethoxy.

The term "haloalkoxyalkyl" as used herein, means a haloalkoxy group, as defined herein, appended to the parent moiety through an alkylene group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Non-limiting examples of monocyclic heterocycles include azetidinyl (including, but not limited thereto, azetidin-2-yl), azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl (including, but not limited thereto, oxetan-2-yl), piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydrobenzothienyl, and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic and the bicyclic heterocycles can contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings can optionally be oxidized and the nitrogen atoms can optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring can contain one heteroatom selected from O or S; or one, two, three, or four nitrogen atoms and optionally one oxygen or one sulfur atom. The six-membered ring contains three double bonds and one, two, three or four nitrogen atoms.

Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, or sulfur atom.

The term "hydroxyl" or "hydroxy" means a —OH group.

The term "hydroxyalkyl" as used herein, means an hydroxy group, as defined herein, appended to the parent moiety through an alkylene group, as defined herein.

The term "oxo" as used herein, means a =O group.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "modulate" refers to the ability of a compound to increase or decrease the function, or activity, of $CB_2$ receptor. "Modulation", as used herein in its various forms, is intended to encompass antagonism, agonism, partial antagonism and/or partial agonism of the activity associated with $CB_2$ receptor.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. COMPOUNDS

Compounds of formula (I) are as described above.

Particular values of variable groups in compounds of formula (I) are as follows. Such values can be used where appropriate with any of the other values, definitions, claims or embodiments defined hereinbefore or hereinafter.

$A^1$ is formula (a), (b), or (c).

In certain embodiments, $A^1$ is formula (a). Thus, included herein, but not limited to, are compounds of formula (I-a)

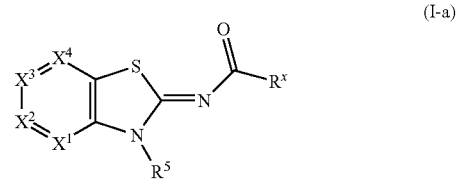

(I-a)

wherein $X^1$, $X^2$, $X^3$, $X^4$, $R^x$, and $R^5$ are as described in the Summary and in embodiments herein below.

Certain embodiments of compounds of formula (I) and (I-a) are directed to those wherein $X^4$ is N, $X^3$ is $CR^3$, $X^2$ is $CR^2$, $X^1$ is N, and $R^2$ and $R^3$ are as disclosed in the Summary and herein. In conjunction with any one of the embodiments described herein below, $R^2$ and $R^3$ are the same or different, and are, for example, each independently hydrogen, alkyl (e.g. $C_1$-$C_6$ alkyl such as, but not limited to, methyl), or hydroxy. In conjunction with any one of the embodiments described herein below, $R^2$ and $R^3$ are, for example, hydrogen.

Certain embodiments of compounds of formula (I) and (I-a) are directed to those wherein $X^4$ is N, $X^3$ is $CR^3$, $X^2$ is N, $X^1$ is $CR^1$, and $R^1$ and $R^3$ are as disclosed in the Summary and herein. In conjunction with any one of the embodiments described herein below, $R^1$ and $R^3$ are the same or different, and are, for example, each independently hydrogen, alkyl (e.g. $C_1$-$C_6$ alkyl such as, but not limited to, methyl), or hydroxy. In conjunction with any one of the embodiments described herein below, for example, $R^1$ is hydroxy or hydrogen, and $R^3$ is hydrogen.

In certain embodiments, $A^1$ is formula (b). Thus, included herein, but not limited to, are compounds of formula (I-b)

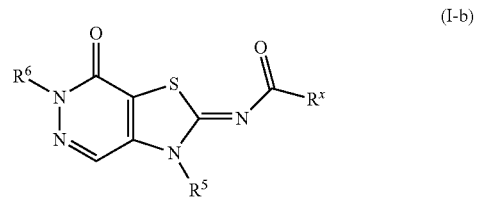

(I-b)

wherein $R^5$, $R^x$, and $R^6$ are as described in the Summary and in embodiments herein below. In conjunction with any of the below embodiments, $R^6$, for example, is $C_1$-$C_6$ alkyl (such as, but not limited to, methyl).

In certain embodiments, $A^1$ is formula (c). Thus, included herein, but not limited to, are compounds of formula (I-c)

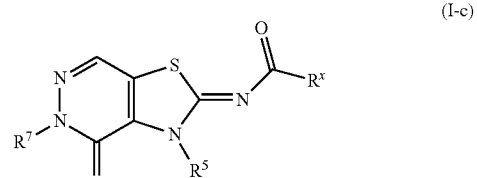

(I-c)

wherein $R^5$, $R^x$, and $R^7$ are as described in the Summary and in embodiments herein below. In conjunction with any of the below embodiments, $R^7$, for example, is $C_1$-$C_6$ alkyl (such as, but not limited to, methyl).

$R^5$ for compounds of formula (I), (I-a), (I-b), and (I-c) has values as disclosed in the Summary. Certain embodiments are directed to a group of compounds of formula (I), (I-a), (I-b), or (I-c) wherein $R^5$ is $C_2$-$C_{10}$ alkyl (e.g. $C_3$-$C_4$ alkyl such as but not limited to, isobutyl, n-butyl, n-propyl), alkenyl (e.g. but-2,3-dienyl), alkynyl (e.g. but-3-ynyl), haloalkyl (e.g., 3,3,3-trifluoropropyl, 4,4,4-trifluorobutyl), —$(CR^{5a}R^{5b})_{q4}$—O-haloalkyl or $(CR^{5a}R^{5b})_{q5}$-$G^{5b}$. In certain embodiments, $R^5$ is $C_2$-$C_{10}$ alkyl (e.g. isobutyl, n-butyl, n-propyl, but not limited thereto), haloalkyl (e.g. 3,3,3-trifluoropropyl, 4,4,4-trifluorobutyl), or —$(CR^{5a}R^{5b})_{q5}$-$G^{5b}$. In certain embodiments, $R^5$ is $C_2$-$C_{10}$ alkyl (e.g. isobutyl, n-butyl, n-propyl, but not limited thereto) or haloalkyl (e.g. 3,3,3-trifluoropropyl, 4,4,4-trifluorobutyl). In certain embodiments, $R^5$ is $C_2$-$C_{10}$ alkyl (e.g. isobutyl, n-butyl, n-propyl, but not limited thereto). In other embodiments, $R^5$ is —$(CR^{5a}R^{5b})_{q5}$-$G^{5b}$. In yet other embodiments, $R^5$ is $C_2$-$C_{10}$ alkyl (e.g. isobutyl, n-butyl, n-propyl, but not limited thereto) or —$(CR^{5a}R^{5b})_{q5}$-$G^{5b}$. In all these embodiments, $R^{5a}$, $R^{5b}$, q4, q5, and $G^{5b}$ are as described in the Summary and herein. For example, $G^{5b}$ is an optionally substituted monocyclic ring selected from the group consisting of cycloalkyl, cycloalkenyl, thien-2-yl, and thien-3-yl. In certain embodiments, $G^{5b}$ is an optionally substituted monocyclic cycloalkyl (e.g. cyclopropyl, cyclobutyl, cyclopentyl, but not limited thereto). Each of these rings of $G^{5b}$ is independently unsubstituted or substituted as described in the Summary and herein. In conjunction with any of the above or below embodiments, for example, each of these rings can be unsubstituted or substituted with 1 or 2 groups selected from alkyl such as, but not limited to, $C_1$-$C_4$ alkyl (e.g. methyl), halogen (e.g. F), haloalkyl, oxo, hydroxy, alkoxy (including, but not limited to $OCH_3$), and haloalkoxy. In conjunction with any of the above or below embodiments, $R^{5a}$ and $R^{5b}$, for example, are each independently hydrogen or $C_1$-$C_4$ alkyl (e.g. methyl). In conjunction with any of the above or below embodiments, $R^{5a}$ and $R^{5b}$, for example, are hydrogen. q4, for example, is 2 or 3. q5, for example, is 1, 2, or 3. In certain embodiments wherein $R^5$ is —$(CR^{5a}R^{5b})_{q5}$-$G^{5b}$, then $R^{5a}$ and $R^{5b}$ are hydrogen and q5 is 1.

$R^x$ for compounds of formula (I), (I-a), (I-b), and (I-c) has values as disclosed in the Summary. In certain embodiments, $R^x$ is aryl (e.g. optionally substituted phenyl) or heteroaryl, each of which is optionally substituted. In other embodiments, $R^x$ is optionally substituted aryl (e.g. optionally substituted phenyl). In yet other embodiments, $R^x$ is optionally substituted heteroaryl (e.g. optionally substituted pyridinyl or quinolinyl). In yet other embodiments, $R^x$ is optionally substituted monocyclic heteroaryl (e.g. optionally substituted pyridinyl).

The optional substituents of $R^x$ are as described in the Summary and embodiments herein. In conjunction with any of the above and below embodiments, $R^x$ is unsubstituted or substituted with one, two, or three (for example, one or two) substituents selected from the group consisting of alkyl, alkenyl, alkynyl, halogen, haloalkyl, —CN, $NO_2$, —$OR^a$, and —$S(O)_2R^e$ wherein $R^a$ and $R^e$ are as described in the Summary and embodiments herein. $R^e$, for example, is $C_1$-$C_6$ alkyl or haloalkyl. $R^a$, for example, is $G^a$, —$(CR^{1c}R^{1d})_{q2}$-$G^a$, —$(CR^{1c}R^{1d})_{q4}$—$OR^b$, $N(R^d)C(O)R^c$, $N(R^d)C(O)OR^c$, $N(R^d)C(O)N(R^d)_2$, $N(R^d)_2$, or $N=C(R^p)(R^q)$. In certain embodiments, $R^a$, for example, is —$(CR^{1c}R^{1d})_{q4}$—$OR^b$. $G^a$, $R^{1c}$, $R^{1d}$, q2, q4, $R^b$, $R^c$, $R^d$, $R^p$, and $R^q$ are as described in the Summary and embodiments herein. $G^a$, for example, is optionally substituted cycloalkyl (e.g. optionally substituted monocyclic cycloalkyl such as, but not limited to, cyclopropyl and cyclobutyl, each of which is optionally substituted) or optionally substituted heterocycle (e.g. optionally substituted monocyclic heterocycle such as, but not limited to, azetidinyl, pyrrolidinly, each of which is optionally substituted). $R^{1e}$ and $R^{1d}$, for example, are hydrogen or $C_1$-$C_6$ alkyl (e.g. methyl, ethyl). q4, for example, is 2 or 3. $R^b$, for example, is hydrogen, $C_1$-$C_6$ alkyl, or $C_1$-$C_4$ haloalkyl. In certain embodiments, $R^b$ is hydrogen. $R^d$, at each occurrence, can be the same or different, and is independently hydrogen or $C_1$-$C_4$ alkyl (e.g. methyl, isopropyl, tert-butyl).

In conjunction with any of the above or below embodiments when $R^x$ is substituted, it is substituted with at least two substituents wherein one of the substituents of $R^x$ is —$OR^a$ and $R^a$ is —$(CR^{1c}R^{1d})_{q4}$—$OR^b$. The other substituents of $R^x$ are selected from the group consisting of alkyl, alkenyl, alkynyl, halogen, haloalkyl, —CN, $NO_2$, and —$S(O)_2R^e$; wherein $R^e$ is $C_1$-$C_6$ alkyl (e.g. methyl, ethyl, isopropyl). $R^b$, $R^{1c}$, $R^{1d}$, and q4 are as disclosed in the Summary and in the preceding paragraph.

In conjunction with any of the above or below embodiments when $R^x$ is substituted, it is substituted with at least two substituents wherein one of the substituents of $R^x$ is —$OR^a$, $R^a$ is —$(CR^{1c}R^{1d})_{q4}$—$OR^b$; and —$OR^a$ is situated on the ortho carbon atom of $R^x$. The other substituents of $R^x$ are selected from the group consisting of alkyl, alkenyl, alkynyl, halogen, haloalkyl, —CN, $NO_2$, and —$S(O)_2R^e$; wherein $R^e$ is $C_1$-$C_6$ alkyl (e.g. methyl, ethyl, isopropyl). $R^b$, $R^{1c}$, $R^{1d}$, and q4 are as disclosed in the Summary and in the preceding paragraph;

It is appreciated that contemplated herein are compounds of formula (I), (I-a), (I-b), and (I-c) with combinations of the above embodiments, including particular, more particular and preferred embodiments.

Accordingly, one aspect is directed to a group of compounds of formula (I) or (I-a) wherein $X^4$ is N, $X^3$ is $CR^3$, $X^2$ is $CR^2$, $X^1$ is N, $R^x$ is aryl (e.g. optionally substituted phenyl) or heteroaryl, each of which is optionally substituted; $R^2$, $R^3$, and the optional substituents of $R^x$ are as disclosed in the Summary and herein above.

Another aspect is directed to a group of compounds of formula (I) or (I-a) wherein $X^4$ is N, $X^3$ is $CR^3$, $X^2$ is $CR^2$, $X^1$ is N, $R^x$ is optionally substituted aryl (e.g. optionally substituted phenyl); $R^2$, $R^3$, and the optional substituents of $R^x$ are as disclosed in the Summary and herein above.

Another aspect is directed to a group of compounds of formula (I) or (I-a) wherein $X^4$ is N, $X^3$ is $CR^3$, $X^2$ is $CR^2$, $X^1$ is N, $R^x$ is optionally substituted heteroaryl (e.g. optionally substituted monocyclic heteroaryl such as, but not limited to, optionally substituted pyridinyl); $R^2$, $R^3$, and the optional substituents of $R^x$ are as disclosed in the Summary and herein above.

Another aspect is directed to a group of compounds of formula (I) or (I-a) wherein $X^4$ is N, $X^3$ is $CR^3$, $X^2$ is N, $X^1$ is $CR^1$, $R^x$ is aryl (e.g. optionally substituted phenyl) or heteroaryl, each of which is optionally substituted; $R^1$, $R^3$, and the optional substituents of $R^x$ are as disclosed in the Summary and herein above.

Another aspect is directed to a group of compounds of formula (I) or (I-a) wherein $X^4$ is N, $X^3$ is $CR^3$, $X^2$ is N, $X^1$ is $CR^1$, $R^x$ is optionally substituted aryl (e.g. optionally substituted phenyl); $R^1$, $R^3$, and the optional substituents of $R^x$ are as disclosed in the Summary and herein above.

Another aspect is directed to a group of compounds of formula (I) or (I-a) wherein $X^4$ is N, $X^3$ is $CR^3$, $X^2$ is N, $X^1$ is $CR^1$, $R^x$ is optionally substituted heteroaryl (e.g. optionally substituted monocyclic heteroaryl such as, but not limited to, optionally substituted pyridinyl); $R^1$, $R^3$, and the optional substituents of $R^x$ are as disclosed in the Summary and herein above.

Another aspect is directed to a group of compounds of formula (I) or (I-b) wherein $R^6$ is $C_1$-$C_6$ alkyl (such as, but not limited, methyl), $R^x$ is aryl (e.g. optionally substituted phenyl) or heteroaryl, each of which is optionally substituted; and the optional substituents of $R^x$ are as disclosed in the Summary and herein above.

Another aspect is directed to a group of compounds of formula (I) or (I-b) wherein $R^6$ is $C_1$-$C_6$ alkyl (such as, but not limited, methyl), $R^x$ is optionally substituted aryl (e.g. optionally substituted phenyl); and the optional substituents of $R^x$ are as disclosed in the Summary and herein above.

Another aspect is directed to a group of compounds of formula (I) or (I-b) wherein $R^6$ is $C_1$-$C_6$ alkyl (such as, but not limited, methyl), $R^x$ is optionally substituted heteroaryl (e.g. optionally substituted monocyclic heteroaryl such as, but not limited to, optionally substituted pyridinyl); and the optional substituents of $R^x$ are as disclosed in the Summary and herein above.

Another aspect is directed to a group of compounds of formula (I) or (I-c) wherein $R^7$ is $C_1$-$C_6$ alkyl (such as, but not limited, methyl), $R^x$ is aryl (e.g. optionally substituted phenyl) or heteroaryl, each of which is optionally substituted; and the optional substituents of $R^x$ are as disclosed in the Summary and herein above.

Another aspect is directed to a group of compounds of formula (I) or (I-c) wherein $R^7$ is $C_1$-$C_6$ alkyl (such as, but not limited, methyl), $R^x$ is optionally substituted aryl (e.g. optionally substituted phenyl); and the optional substituents of $R^x$ are as disclosed in the Summary and herein above.

Another aspect is directed to a group of compounds of formula (I) or (I-c) wherein $R^7$ is $C_1$-$C_6$ alkyl (such as, but not limited, methyl), $R^x$ is optionally substituted heteroaryl (e.g. optionally substituted monocyclic heteroaryl such as, but not limited to, optionally substituted pyridinyl); and the optional substituents of $R^x$ are as disclosed in the Summary and herein above.

Within each of the groups of compounds of formula (I), (I-a), (I-b), and (I-c) disclosed in the preceding paragraphs, $R^5$ has values as disclosed in the Summary and embodiments herein above.

Thus, within each group of compounds of formula (I), (I-a), (I-b), and (I-c), examples of a subgroup include, but are not limited to, those wherein $R^5$ is $C_2$-$C_{10}$ alkyl (e.g. $C_3$-$C_4$ alkyl such as, but not limited to, isobutyl, n-butyl, n-propyl), alkenyl (e.g. but-2,3-dienyl), alkynyl (e.g. but-3-ynyl), haloalkyl (e.g. 3,3,3-trifluoropropyl, 4,4,4-trifluorobutyl), —$(CR^{5a}R^{5b})_{q4}$—O-haloalkyl, or —$(CR^{5a}R^{5b})_{q5}$-$G^{5b}$ wherein $R^{5a}$, $R^{5b}$, q4, q5, and $G^{5b}$ are as described in the Summary and the embodiments herein.

Other examples of a subgroup include, but are not limited to, those wherein $R^5$ is $C_2$-$C_{10}$ alkyl (e.g. $C_3$-$C_4$ alkyl such as, but not limited to, isobutyl, n-butyl, n-propyl), haloalkyl (e.g. 3,3,3-trifluoropropyl, 4,4,4-trifluorobutyl), or —$(CR^{5a}R^{5b})_{q5}$-$G^{5b}$ wherein $R^{5a}$, $R^{5b}$, q5, and $G^{5b}$ are as described in the Summary and the embodiments herein.

Yet other examples of a subgroup include, but are not limited to, those wherein $R^5$ is $C_2$-$C_{10}$ alkyl (e.g. $C_3$-$C_4$ alkyl such as, but not limited to, isobutyl, n-butyl, n-propyl) or —$(CR^{5a}R^{5b})_{q5}$-$G^{5b}$ wherein $R^{5a}$, $R^{5b}$, q5, and $G^{5b}$ are as described in the Summary and the embodiments herein.

Yet other examples of a subgroup include, but are not limited to, those wherein $R^5$ is $C_2$-$C_{10}$ alkyl (e.g. $C_3$-$C_4$ alkyl such as, but not limited to, isobutyl, n-butyl, n-propyl) or haloalkyl (e.g. 3,3,3-trifluoropropyl, 4,4,4-trifluorobutyl).

Yet other examples of a subgroup include, but are not limited to, those wherein $R^5$ is $C_2$-$C_{10}$ alkyl (e.g. $C_3$-$C_4$ alkyl such as, but not limited to, isobutyl, n-butyl, n-propyl).

Further examples of a subgroup include, but are not limited to, those wherein $R^5$ is —$(CR^{5a}R^{5b})_{q5}$-$G^{5b}$, and $R^{5a}$, $R^{5b}$, q5, and $G^{5b}$ are as described in the Summary and the embodiments herein.

Yet further examples of a subgroup include, but are not limited to, those wherein $R^5$ is —$(CH_2)$-$G^{5b}$ and $G^{5b}$ is as described generally in the Summary and in embodiments herein.

For each of the above groups and subgroups of compounds described, $G^{5b}$, for example, is an optionally substituted monocyclic ring selected from the group consisting of cycloalkyl, cycloalkenyl, thien-2-yl, and thien-3-yl. In certain embodiments, $G^{5b}$ is an optionally substituted monocyclic cycloalkyl (e.g. cyclopropyl, cyclobutyl, but not limited thereto). Each of these exemplary rings of $G^{5b}$ is independently unsubstituted or substituted as described in the Summary. For example, each can be unsubstituted or substituted with 1 or 2 groups selected from alkyl such as, but not limited to, $C_1$-$C_4$ alkyl (e.g. methyl), halogen (e.g. F), haloalkyl, oxo, hydroxy, alkoxy (including, but not limited to $OCH_3$), and haloalkoxy. $R^{5a}$ and $R^{5b}$ are, for example, hydrogen or $C_1$-$C_4$ alkyl (e.g. methyl).

Further examples of compounds of formula (I) include those wherein $R^x$ is a phenyl or heteroaryl, each of which is substituted with 2 substituents independently selected from the group consisting of halogen, haloalkyl, —$OR^a$, —$OC(O)R^e$, —$C(O)R^f$, —$C(O)OR^f$, $(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;

$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;

$R^5$, at each occurrence, is the same or different, and is independently $C_2$-$C_{10}$ alkyl, alkenyl, alkynyl, or haloalkyl; and $R^{1a}$, $R^{1b}$, $R^{1c}$, $R^{1d}$, q1, q2, q4, $R^a$, $R^b$, $R^e$, $R^f$, and ring $A^1$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein $A^1$ is formula (a);

$R^x$ is a phenyl or heteroaryl, each of which is substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a(CR^{1a}R^{1b})_{q1}$—$OC(O)R^e$, —$(CR^{1a}R^{1b})_{q1}$—$C(O)R^f$, and —$(CR^{1a}R^{1b})C(O)OR^f$;

$R^a$ is —$(CR^{1c}R^{1d})_{q2}$—$C(O)R^b$—$(CR^{1c}R^{1d})_{q4}$—$OR^b$, or —$(CR^{1c}R^{1d})_{q2}$—$OC(O)R^b$;

$R^5$ is $C_2$-$C_{10}$ alkyl, alkenyl, alkynyl, or haloalkyl; and $R^{1a}$, $R^{1b}$, $R^{1c}$, $R^{1d}$, q1, q2, q4, $R^a$, $R^b$, $R^e$, $R^f$, $X^1$, $X^2$, $X^3$, and $X^4$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein $A^1$ is formula (a);

$X^4$ is N, $X^3$ is $CR^3$, $X^2$ is $CR^2$, $X^1$ is N;

$R^x$ is a phenyl or heteroaryl, each of which is substituted with 2 substituents independently selected from the group consisting of halogen, haloalkyl, —$OR^a$, —$OC(O)$ $R^e$, —C(O)$R^f$, —C(O)O$R^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl, alkenyl, alkynyl, or haloalkyl; and $R^2$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein
$A^1$ is formula (a);
$X^4$ is N, $X^3$ is CR$^3$, $X^2$ is CR$^2$, $X^1$ is N;
$R^x$ is a phenyl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$^{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl, alkenyl, alkynyl, or haloalkyl; and $R^2$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein
$A^1$ is formula (a);
$X^4$ is N, $X^3$ is CR$^3$, $X^2$ is CR$^2$, $X^1$ is N;
$R^x$ is a phenyl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl; and $R^2$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein
$A^1$ is formula (a);
$X^4$ is N, $X^3$ is CR$^3$, $X^2$ is CR$^2$, $X^1$ is N;
$R^x$ is a heteroaryl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl, alkenyl, alkynyl, or haloalkyl; and $R^2$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein
$A^1$ is formula (a);
$X^4$ is N, $X^3$ is CR$^3$, $X^2$ is CR$^2$, $X^1$ is N;
$R^x$ is a heteroaryl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl; and $R^2$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein
$A^1$ is formula (a);
$X^4$ is N, $X^3$ is CR$^3$, $X^2$ is N, $X^1$ is CR$^1$;
$R^x$ is a phenyl or heteroaryl, each of which is substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$—(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl, alkenyl, alkynyl, or haloalkyl; and $R^1$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein
$A^1$ is formula (a);
$X^4$ is N, $X^3$ is CR$^3$, $X^2$ is N, $X^1$ is CR$^1$;
$R^x$ is a phenyl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl, alkenyl, alkynyl, or haloalkyl; and $R^1$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein
$A^1$ is formula (a);
$X^4$ is N, $X^3$ is CR$^3$, $X^2$ is N, $X^1$ is CR$^1$;
$R^x$ is a phenyl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q2}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl; and $R^1$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein
$A^1$ is formula (a);
$X^4$ is N, $X^3$ is CR$^3$, $X^2$ is N, $X^1$ is CR$^1$;
$R^x$ is a heteroaryl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

$R^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

$R^5$ is C$_2$-C$_{10}$ alkyl, alkenyl, alkynyl, or haloalkyl; and $R^1$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein $A^1$ is formula (a);
$X^4$ is N, $X^3$ is $CR^3$, $X^2$ is N, $X^1$ is $CR^1$;
$R^x$ is a heteroaryl substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^1)_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl; and
$R^1$, $R^3$, $R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein $A^1$ is formula (b);
$R^x$ is a phenyl or heteroaryl, each of which is substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl, alkenyl, alkynyl, or haloalkyl; and
$R^{1a}$, $R^{1b}$, $R^{1c}$, $R^{1d}$, q1, q2, q4, $R^a$, $R^b$, $R^e$, $R^f$, and $R^6$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein $A^1$ is formula (b);
$R^6$ is $C_1$-$C_6$ alkyl;
$R^x$ is a phenyl or heteroaryl, each of which is substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl, alkenyl, alkynyl, or haloalkyl; and
$R^{1a}$, $R^{1b}$, $R^{1c}$, $R^{1d}$, q1, q2, q4, $R^a$, $R^b$, $R^e$, and $R^f$ have meanings as described in the Summary section. In certain embodiments, the heteroaryl of $R^x$ is a monocyclic heteroaryl. In yet other embodiments, the heteroaryl of $R^x$ is pyridinyl.

Other examples of compounds of formula (I) include those wherein $A^1$ is formula (b);
$R^6$ is $C_1$-$C_6$ alkyl;
$R^x$ is a phenyl substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;

$R^5$ is $C_2$-$C_{10}$ alkyl, alkenyl, alkynyl, or haloalkyl; and
$R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein $A^1$ is formula (b);
$R^6$ is $C_1$-$C_6$ alkyl;
$R^x$ is a phenyl substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl; and
$R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein $A^1$ is formula (c);
$R^x$ is a phenyl or heteroaryl, each of which is substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl, alkenyl, alkynyl, or haloalkyl; and
$R^{1a}$, $R^{1b}$, $R^{1c}$, $R^{1d}$, q1, q2, q4, $R^a$, $R^b$, $R^e$, $R^f$, and $R^7$ have meanings as described in the Summary section.

Other examples of compounds of formula (I) include those wherein $A^1$ is formula (c);
$R^7$ is $C_1$-$C_6$ alkyl;
$R^x$ is a phenyl or heteroaryl, each of which is substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})^{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl, alkenyl, alkynyl, or haloalkyl; and
$R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein $A^1$ is formula (c);
$R^7$ is $C_1$-$C_6$ alkyl;
$R^x$ is a phenyl substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$—$OR^a$, —$(CR^{1a}R^{1b})_{q1}$—$OC(O)R^e$, —$(CR^{1a}R^{1b})_{q1}$—$C(O)R^f$, and —$(CR^{1a}R^{1b})_{q1}$—$C(O)OR^f$;
$R^a$ is —$(CR^{1c}R^{1d})_{q2}$—$C(O)R^b$, —$(CR^{1c}R^{1d})_{q4}$—$OR^b$, or —$(CR^{1c}R^{1d})_{q2}$—$OC(O)R^b$;
$R^5$ is $C_2$-$C_{10}$ alkyl, alkenyl, alkynyl, or haloalkyl; and
$R^{1a}$, $R^{1b}$, $R^{1c}$, $R^{1d}$, q1, q2, q4, $R^a$, $R^b$, $R^e$, and $R^f$ have meanings as described in the Summary section.

Other examples of compounds of formula (I) include those wherein $A^1$ is formula (c);
$R^7$ is $C_1$-$C_6$ alkyl;
$R^x$ is a phenyl substituted with 2 substituents independently selected from the group consisting of halogen, haloalkyl, —$OR^a$, —$OC(O)R^e$, —$C(O)R^f$, —$C(O)OR^f$, —$(CR^{1a}R^{1b})_{q1}$ —OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

R$^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

R$^5$ is C$_2$-C$_{10}$ alkyl; and

R$^{1a}$, R$^{1b}$, R$^{1c}$, R$^{1d}$, q1, q2, q4, R$^a$, R$^b$, R$^e$, and R$^f$ have meanings as described in the Summary section.

Other examples of compounds of formula (I) include those wherein R$^x$ is a phenyl or heteroaryl, each of which is substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

R$^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

R$^5$, at each occurrence, is the same or different, and is independently C$_2$-C$_{10}$ alkyl or haloalkyl; and R$^{1a}$, R$^{1b}$, R$^{1c}$, R$^{1d}$, q1, q2, q4, R$^a$, R$^b$, R$^e$, R$^f$, and ring A$^1$ have meanings as described in the Summary section. In certain embodiments, R$^5$ is C$_2$-C$_{10}$ alkyl.

Other examples of compounds of formula (I) include those wherein R$^x$ is a phenyl substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—OR$^a$, —(CR$^{1a}$R$^{1b}$)$_{q1}$—OC(O)R$^e$, —(CR$^{1a}$R$^{1b}$)$_{q1}$—C(O)R$^f$, and —(CR$^{1a}$R$^{1b}$)$_{q1}$—C(O)OR$^f$;

R$^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

R$^5$ is C$_2$-C$_{10}$ alkyl or haloalkyl; and

R$^{1a}$, R$^{1b}$, R$^{1c}$, R$^{1d}$, q1, q2, q4, R$^a$, R$^b$, R$^e$, R$^f$, and ring A$^1$ have meanings as described in the Summary section. In certain embodiments, R$^5$ is C$_2$-C$_{10}$ alkyl.

Exemplary compounds include, but are not limited to:

N-[(2Z)-1-butyl-7-hydroxy[1,3]thiazolo[5,4-d]pyrimidin-2(1H)-ylidene]-2-{[(2S)-2-hydroxypropyl]oxy}-5-(trifluoromethyl)benzamide;

N-[(2Z)-3-butyl[1,3]thiazolo[4,5-b]pyrazin-2(3H)-ylidene]-2-{[(2S)-2-hydroxypropyl]oxy}-5-(trifluoromethyl)benzamide;

N-[(2Z)-1-butyl[1,3]thiazolo[5,4-d]pyrimidin-2(1H)-ylidene]-2-{[(2S)-2-hydroxypropyl]oxy}-5-(trifluoromethyl)benzamide;

N-[(2Z)-3-butyl-5-methyl-4-oxo-4,5-dihydro[1,3]thiazolo[4,5-d]pyridazin-2(3H)-ylidene]-2-{[(2S)-2-hydroxypropyl]oxy}-5-(trifluoromethyl)benzamide;

N-[(2Z)-3-butyl-6-methyl-7-oxo-6,7-dihydro[1,3]thiazolo[4,5-d]pyridazin-2(3H)-ylidene]-2-{[(2S)-2-hydroxypropyl]oxy}-5-(trifluoromethyl)benzamide;

N-[(2Z)-1-butyl[1,3]thiazolo[5,4-d]pyrimidin-2(1H)-ylidene]-6-chloro-4-(trifluoromethyl)pyridine-3-carboxamide;

N-[(2Z)-3-butyl[1,3]thiazolo[4,5-b]pyrazin-2(3H)-ylidene]-6-chloro-4-(trifluoromethyl)pyridine-3-carboxamide; and N-[(2Z)-3-butyl-5-methyl-4-oxo-4,5-dihydro[1,3]thiazolo[4,5-d]pyridazin-2(3H)-ylidene]-2-(2-hydroxy-2-methylpropoxy)-5-(trifluoromethyl)benzamide.

Present compounds can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers can be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein can exhibit the phenomenon of tautomerism. The formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Present compounds can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as D$_2$SO$_4$/D$_2$O. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of CB2 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compounds prove to be toxic or carcinogenic (Foster et al., Advances in Drug Research Vol. 14, pp. 2-36, Academic press, London, 1985; Kato et al., *J. Labeled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to CB2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D Metal., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions potentially altering the pharmacokinetic profile or efficacy relative to the non-isotopic compound.

c. BIOLOGICAL DATA (i) In Vitro Methods—$CB_2$ Radioligand Binding Assay:

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μL/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP 55,940 ranging from 0.01 to 8 nM. Competition experiments were conducted with 0.5 nM [$^3$H]CP 55,940 and five concentrations (0.01 nM to 10 μM) of displacing ligands. The addition of 10 μM unlabeled CP 55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 μg/well for rat $CB_2$) into wells of a deep well plate containing [$^3$H]CP 55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP 55,940 ranging from 0.01 to 8 nM. Competition experiments were conducted with 0.5 nM [$^3$H] CP 55,940 and five concentrations of displacing ligands selected from the range of 0.01 nM to 10 μM. The addition of 10 μM unlabeled CP 55,940 (Tocris, Ellisville, Mo.) was used to assess nonspecific binding.

Certain compounds tested with the above assay have equilibrium dissociation constants ($K_i$) of less than about 1,000 nM, for example, less than about 400 nM, or less than about 200 nM, or less than about 100 nM.

TABLE 1

| Example | human $CB_2$ binding ($K_i$, nM) | rat $CB_2$ binding ($K_i$, nM) |
|---|---|---|
| 1 | 233 | 157 |
| 2 | 2.0 | 4.1 |
| 3 | 10 | 4.0 |
| 4 | 36 | 5.0 |
| 5 | 6.2 | 1.5 | d. METHODS OF USING THE COMPOUNDS

One embodiment provides methods for treating pain (for example, chronic pain, neuropathic pain, nociceptive pain, migraine, post-stroke pain, spinal cord injury, multiple sclerosis pain, osteoarthritric pain, inflammatory pain, cancer pain, lower back pain, post operative pain, diabetic neuropathic pain, migraine, fibromyalgia, post herpatic neuralgia, phantom limb pain, and eye pain, or combinations thereof) in a mammal (including human) in need of such treatment. The methods comprise administering to the mammal a therapeutically effective amount of a compound as described herein, or a pharmaceutically acceptable salt, solvate, or salt of a solvate thereof, alone or in combination with a pharmaceutically acceptable carrier. The method further comprises administration of the present compounds as a single dose. The method also comprises repeated or chronic administration of the present compounds over a period of days, weeks, months, or longer. In certain embodiments, the method comprises administering to the mammal a therapeutically effective amount of a compound as described herein, or a pharmaceutically acceptable salt, solvate, or salt of a solvate thereof, in combination with a nonsteroidal anti-inflammatory drugs (NSAIDs), or an analgesic (for example, acetaminophen, opioids), or a combination thereof, alone or in combination with a pharmaceutically acceptable carrier.

Another embodiment provides methods for treating disorders selected from the group consisting of inflammatory disorders, immune disorders, neurological disorders, cancers of the immune system, respiratory disorders, and cardiovascular disorders in a mammal in need of such treatment. The method comprises administering to the mammal therapeutically effective amount of a compound described herein or pharmaceutically acceptable salts, solvates, or salts of solvates thereof, alone or in combination with a pharmaceutically acceptable carrier.

Yet another embodiment relates to methods for providing neuroprotection in a mammal in need of such treatment. These methods comprise administering to the mammal therapeutically effective amounts of compounds described herein or pharmaceutically acceptable salts, solvates, or salts of solvates thereof, alone or in combination with a pharmaceutically acceptable carrier.

Another embodiment provides method for increasing the therapeutic effectiveness or potency of compounds described herein by repeated or chronic administration of present compounds or pharmaceutical compositions thereof over a period of days, weeks, or months.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators can be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system.—Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands can be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators can provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators can possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators can represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators can represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators can have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators can be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor can be clinically useful for the treatment of atherosclerosis.

$CB_2$ receptors are expressed on malignant cells of the immune system and targeting $CB_2$ receptors to induce apoptosis can constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators can have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators can have utility for the treatment or prophylaxis of cardiovascular disease and the development of myocardial infarction.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level can depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the compounds can be required to achieve the desired therapeutic response. "Repeated or chronic administration" refers to the administration of the compounds daily (i.e., every day) or intermittently (i.e., not every day) over a period of days, weeks, months, or longer. In particular, the treatment of chronic painful conditions is anticipated to require such repeated or chronic administration of compounds described herein. The compounds can become more effective upon repeated or chronic administration such that the therapeutically effective doses on repeated or chronic administration can be lower than the therapeutically effective dose from a single administration.

Compounds can also be administered as a pharmaceutical composition comprising the compounds of interest, or pharmaceutically acceptable salts, solvates, or salts of solvates thereof, in combination with pharmaceutically acceptable carriers. The phrase "therapeutically effective amount" of a compound means a sufficient amount of the compound to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The compounds can be administered alone, or in combination with one or more other compounds described herein, or in combination (i.e. co-administered) with one or more additional pharmaceutical agents. For example, one or more compounds, or pharmaceutically acceptable salts, solvates, or salts of solvates thereof, can be administered in combination with an analgesic (e.g. acetaminophen, opioid such as morphine), or with a nonsteroidal anti-inflammatory drug (NSAIDs), or combinations thereof. Non-limiting examples of NSAIDs include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, can be administered to the patient together, in a single oral dosage composition having a fixed ratio of each active ingredient, such as a tablet or capsule; or each agent can be administered in separate oral dosage formulations.

Where separate dosage formulations are used, the compounds and one or more additional pharmaceutical agents can be administered at essentially the same time (e.g., concurrently) or at separately staggered times (e.g., sequentially).

The total daily dose of the compounds administered to a human or other animal range from about 0.01 mg/kg body weight to about 100 mg/kg body weight, for example, in the range of from about 0.03 mg/kg body weight to about 30 mg/kg body weight. If desired, the effective daily dose can be divided into multiple doses for purposes of administration. Consequently, single dose compositions can contain such amounts or submultiples thereof to make up the daily dose. It is understood that the effective daily dose can vary with the duration of the treatment.

e. PHARMACEUTICAL COMPOSITIONS

Further provided herein are pharmaceutical compositions that comprise one or more compounds described herein, or pharmaceutically acceptable salts, solvates, or salts of solvates thereof, formulated together with a pharmaceutically acceptable carrier.

Another aspect provides pharmaceutical compositions comprising a compound described herein, or a pharmaceutically acceptable salt, solvate, or salt of a solvate thereof, and a pharmaceutically acceptable carrier, alone or in combination with an analgesic (e.g. acetaminophen), or in combination with a nonsteroidal anti-inflammatory drug (NSAIDs), or a combination thereof, formulated together with a pharmaceutically acceptable carrier.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound can be mixed under sterile conditions with a pharmaceutically acceptable carrier and any needed preservatives, buffers or propellants which can be required. Ophthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of the compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds can be prepared by a variety of processes well known for the preparation of compounds of this class. For example, the compounds described herein wherein the groups $X^1$, $X^2$, $X^3$, $X^4$, $R^a$, $R^5$, $R^6$, $R^7$, and $R^x$, have the meanings as set forth in the summary section unless otherwise noted, can be synthesized as shown in Schemes 1 and 2.

Abbreviations which have been used in the descriptions of the Schemes and the Examples that follow are: DIEA for diisopropylethylamine, DMA for dimethylacetamide, DMF for N,N-dimethylformamide, DMSO for dimethyl sulfoxide, EtOAc for ethyl acetate, EtOH for ethanol, $Et_3N$ for triethylamine, KOt-Bu for potassium t-butoxide, MeOH for methanol, THF for tetrahydrofuran, and TBTU for O-benzotriazol-1-yl-N,N,N',N'-tetramethyluronium tetrafluoroborate.

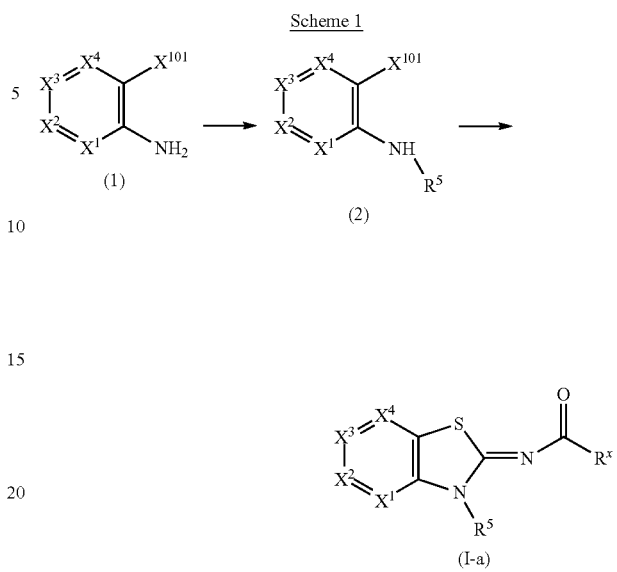

Compounds of formula (I-a) can be prepared using general procedures as shown in Scheme 1 Amines of formula (1) wherein $X^{101}$ is halogen can be treated with halides of formula $R^5X^{102}$ wherein $X^{102}$ is halogen in the presence of a base such as, but not limited to, sodium tert-butoxide to provide compounds of formula (2). The reaction is generally conducted in the presence of a solvent such as, but not limited to, dimethyl acetamide, and at a temperature ranging from about 40° C. to about 100° C.

Compounds of formula (2) can be treated with isothiocyanates of formula $R^xC(O)NCS$ in a solvent such as, but not limited to, dioxane, and at a at a temperature ranging from about 40° C. to about 100° C. to provide compounds of formula (I-a).

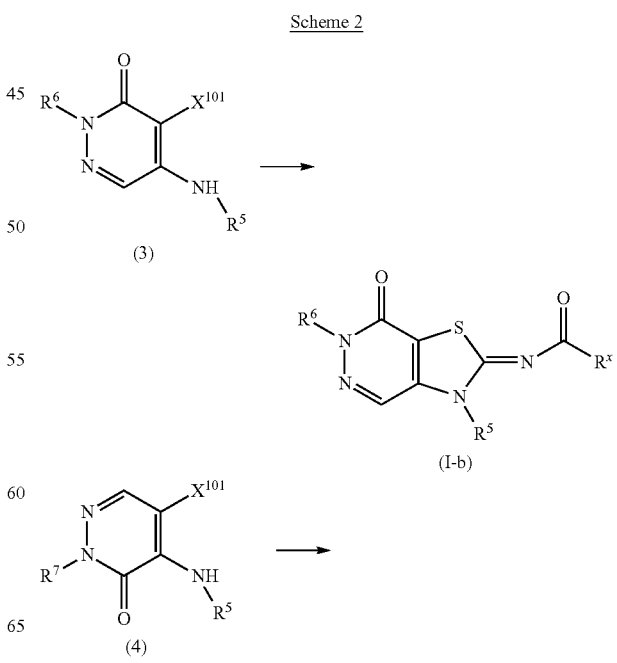

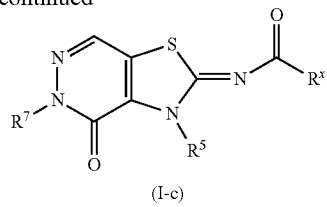

(I-c)

Similarly, compounds of formula (I-b) and (I-c) can be prepared from compounds of formula (3) and (4) respectively with the appropriate isothiocyanates using the general procedures as shown above.

Compounds of formula (I) wherein one of the substituents of $R^x$ is fluorine can be treated with alcohols of formula $R^aOH$ with a base to provide compounds of formula (I) wherein one of the substituents of $R^x$ is —$OR^a$. The reaction is generally conducted in the presence of a base such as, but not limited to, sodium tert-butoxide, potassium tert-butoxide, or sodium hydride, and in a solvent such as, but not limited to, tetrahydrofuran or N,N-dimethylformamide.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

EXAMPLES

Example 1

N-[(2Z)-1-butyl-7-hydroxy[1,3]thiazolo[5,4-d]pyrimidin-2(1H)-ylidene]-2-{[(2S)-2-hydroxypropyl]oxy}-5-(trifluoromethyl)benzamide Example 1A 4-tert-butoxy-N-butyl-6-chloropyrimidin-5-amine A mixture of 4,6-dichloropyrimidin-5-amine (1.64 g, 10 mmol), sodium tert-butoxide (1.92 g, 20 mmol) and 1-iodobutane (2.02 g, 11 mmol) in DMA (30 mL) was heated at 50° C. for 12 hours. The mixture was poured into water, treated with saturated aqueous $NaHCO_3$ and extracted with ethyl acetate. The acetate layer was washed with water, brine, dried with $MgSO_4$, filtered, and concentrated under reduced pressure. The residue was purified by chromatography (hexane-EtOAc 1:1) to afford 200 mg of the title compound. MS (ESI) m/z 258 (M+H)$^+$.

Example 1B

N-[(2Z)-1-butyl-7-hydroxy[1,3]thiazolo[5,4-d]pyrimidin-2(1H)-ylidene]-2-fluoro-5-(trifluoromethyl)benzamide A mixture Example 1A (60 mg, 0.23 mmol) and 2-fluoro-5-(trifluoromethyl)benzoyl isothiocyanate (70 mg, 0.28 mmol) in dioxane was heated at 60° C. for 12 hours. The mixture was concentrated under reduced pressure and the residue was partitioned between ethyl acetate and saturated aqueous $NaHCO_3$. The organic layer was washed with brine, dried with $MgSO_4$, filtered, and concentrated under reduced pressure. The residue was purified by chromatography (EtOAc) to afford 65 mg of the title compound. MS (ESI) m/z 415 (M+H)$^+$.

Example 1C

N-[(2Z)-1-butyl-7-hydroxy[1,3]thiazolo[5,4-d]pyrimidin-2(1H)-ylidene]-2-{[(2S)-2-hydroxypropyl]oxy}-5-(trifluoromethyl)benzamide A mixture of Example 1B (65 mg, 0.16 mmol), (S)-propane-1,2-diol (28 mg, 0.36 mmol) and 1N solution of potassium tert-butoxide in THF (0.33 mL, 0.33 mmol) was heated at 45° C. for 18 hours. The mixture was acidified to pH 5 with acetic acid then concentrated under reduced pressure. The residue was stirred with saturated aqueous $NaHCO_3$, extracted with EtOAc, concentrated, and the residue was purified by chromatography (EtOAc-EtOH 19:1) to afford 50 mg of the title compound. $^1$H NMR (300 MHz, DMSO-d$_6$) δ ppm 0.90-0.96 (m, 3H) 1.19 (d, J=5.76 Hz, 3H) 1.30-1.41 (m, 2H) 1.77-1.86 (m, 2H) 3.93-4.08 (m, 3H) 4.66-4.76 (m, 2H) 4.87 (d, J=4.07 Hz, 1H) 7.36 (d, J=8.82 Hz, 1H) 7.82 (dd, J=8.82, 2.03 Hz, 1H) 8.22 (s, 2H) 13.12 (s, 1H). MS (ESI) m/z 471 (M+H)$^+$.

Example 2

N-[(2Z)-3-butyl[1,3]thiazolo[4,5-b]pyrazin-2(3H)-ylidene]-2-{[(2S)-2-hydroxypropyl]oxy}-5-(trifluoromethyl)benzamide Example 2A N-butyl-3-chloropyrazin-2-amine The title compound was obtained using the method described in Example 1A by replacing 4,6-dichloropyrimidin-5-amine with 3-chloropyrazin-2-amine MS (ESI) m/z 186 (M+H)$^+$.

Example 2B

N-[(2Z)-3-butyl[1,3]thiazolo[4,5-b]pyrazin-2(3H)-ylidene]-2-fluoro-5-(trifluoromethyl)benzamide Example 2A (760 mg, 4.1 mmol) and 2-fluoro-5-(trifluoromethoxy)benzoyl isothiocyanate (1.12 g, 4.50 mmol) were processed as described in Example 3B to afford the title compound. MS (ESI) m/z 399 (M+H)$^+$.

Example 2C

N-[(2Z)-3-butyl[1,3]thiazolo[4,5-b]pyrazin-2(3H)-ylidene]-2-{[(2S)-2-hydroxypropyl]oxy}-5-(trifluoromethyl)benzamide Example 2B (200 mg, 0.50 mmol) and (S)-propane-1,2-diol (115 mg, 1.51 mmol) were processed as described in Example 3C to afford the title compound and 3-butylthiazolo[4,5-b]pyrazin-2(3H)-imine. $^1$H NMR (300 MHz, DMSO-d$_6$) δ ppm 0.93-0.99 (m, 3H) 1.21 (d, J=5.95 Hz, 3H) 1.36-1.45 (m, 2H) 1.81-1.91 (m, 2H) 3.95-4.11 (m, 3H) 4.46 (t, J=7.34 Hz, 2H) 4.87 (d, J=3.97 Hz, 1H) 7.40 (d, J=8.73 Hz, 1H) 7.87 (dd, J=8.72, 2.78 Hz, 1H) 8.32 (d, J=2.38 Hz, 1H) 8.52-8.61 (m, 2H). MS (ESI) m/z 399 (M+H)$^+$. Characterization of 3-butylthiazolo[4,5-b]pyrazin-2(3H)-imine: $^1$H NMR (300 MHz, DMSO-d$_6$) δ ppm 0.80-0.98 (m, 3H) 1.20-1.39 (m, 2H) 1.65 (t, J=7.29 Hz, 2H) 3.85-4.01 (m, 2H) 7.97 (d, J=3.05 Hz, 1H) 8.07 (d, J=3.05 Hz, 1H) 9.18 (s, 1H); MS (ESI$^+$) m/z 209 (M+H)$^+$.

Example 3

N-[(2Z)-1-butyl[1,3]thiazolo[5,4-d]pyrimidin-2(1H)-ylidene]-2-{[(2S)-2-hydroxypropyl]oxy}-5-(trifluoromethyl)benzamide Example 3A 4-bromo-N-butylpyrimidin-5-amine A mixture of 4-bromopyrimidin-5-amine (1 g, 5.75 mmol), sodium tert-butoxide (1.11 g, 11.5 mmol) and 1-iodobutane (1.11 g, 6.03 mmol) in DMA (15 mL) was heated at 60° C. for 15 hours. The mixture was poured into water and extracted with ethyl acetate. The acetate layer was washed with water, brine, dried with MgSO$_4$, filtered, and concentrated under reduced pressure. The residue was purified by chromatography (hexanes-EtOAc 3:1) to afford 300 mg of the title compound. MS (ESI) m/z 230 (M+H)$^+$.

Example 3B

N-[(2Z)-1-butyl[1,3]thiazolo[5,4-d]pyrimidin-2(1H)-ylidene]-2-fluoro-5-(trifluoromethyl)benzamide A mixture of product from Example 3A (270 mg, 1.17 mmol) and 2-fluoro-5-(trifluoromethyl)benzoyl isothiocyanate (322 mg, 1.29 mmol) in dioxane was heated at 60° C. for 12 hours. The mixture was then concentrated under reduced pressure and the residue was partitioned between ethyl acetate and saturated aqueous NaHCO$_3$. The organic layer was washed with brine, dried with MgSO$_4$, filtered, and concentrated under reduced pressure. The residue was purified by chromatography (hexanes-EtOAc 1:2) to afford 380 mg of the title compound. MS (ESI) m/z 399 (M+H)$^+$.

Example 3C

N-[(2Z)-1-butyl[1,3]thiazolo[5,4-d]pyrimidin-2(1H)-ylidene]-2-{[(2S)-2-hydroxypropyl]oxy}-5-(trifluoromethyl)benzamide A mixture Example 3B (180 mg, 0.45 mmol) and (S)-propane-1,2-diol (172 mg, 2.26 mmol) in THF (10 mL) at 0° C. was treated with a 1N solution of potassium tert-butoxide in THF (0.45 mL, 0.45 mmol). The mixture was allowed to warm to room temperature and stirred for 12 hours. The mixture was acidified to pH 5 with acetic acid then concentrated under reduced pressure. The residue was treated with saturated aqueous NaHCO$_3$ and extracted with EtOAc. The ethyl acetate layer was washed with brine, dried with MgSO$_4$, filtered, and concentrated under reduced pressure. The residue was purified by chromatography (EtOAc) to afford 50 mg of the title compound and 1-butylthiazolo[5,4-d]pyrimidin-2 (1H)-imine $^1$H NMR (300 MHz, DMSO-d$_6$) δ ppm 0.94 (t, J=7.29 Hz, 3H) 1.20 (d, J=5.76 Hz, 3H) 1.36-1.48 (m, 2H) 1.83 (t, J=7.29 Hz, 2H) 3.96-4.09 (m, 3H) 4.50 (t, J=7.29 Hz, 2H) 4.86 (d, J=4.07 Hz, 1H) 7.39 (d, J=8.82 Hz, 1H) 7.86 (dd, J=8.99, 2.20 Hz, 1H) 8.30 (d, J=2.37 Hz, 1H) 9.08 (s, 1H) 9.19 (s, 1H). MS (ESI) m/z 455 (M+H)$^+$. Characterization of 1-butylthiazolo[5,4-d]pyrimidin-2(1H)-imine: $^1$H NMR (300 MHz, DMSO-d$_6$) δ ppm 0.90 (t, J=7.29 Hz, 3H) 1.33 (dd, J=15.09, 7.29 Hz, 2H) 1.50-1.71 (m, 2H) 3.92 (t, J=7.29 Hz, 2H) 8.35 (s, 1H) 8.61 (s, 1H) 8.93 (s, 1H); MS (ESI$^+$) m/z 209 (M+H)$^+$.

Example 4

N-[(2Z)-3-butyl-5-methyl-4-oxo-4,5-dihydro[1,3]thiazolo[4,5-d]pyridazin-2(3H)-ylidene]-2-{[(2S)-2-hydroxypropyl]oxy}-5-(trifluoromethyl)benzamide Example 4A 4-(butylamino)-5-chloro-2-methylpyridazin-3(2H)-one and 5-(butylamino)-4-chloro-2-methylpyridazin-3(2H)-one A mixture of 4,5-dichloro-2-methylpyridazin-3(2H)-one (358 mg, 2 mmol) and butan-1-amine (585 mg, 8 mmol) in acetonitrile was refluxed for 16 hours. The mixture was concentrated under reduced pressure, the residue was dissolved in ethyl acetate, washed with water, brine, dried with MgSO$_4$, filtered, and concentrated. Purification of the residue by chromatography (hexanes-EtOAc 1:1) afforded 170 mg of 4-(butylamino)-5-chloro-2-methylpyridazin-3(2H)-one and 260 mg of 5-(butylamino)-4-chloro-2-methylpyridazin-3(2H)-one. MS (ESI) m/z 215 (M+H)$^+$.

Example 4B

N-[(2Z)-3-butyl-5-methyl-4-oxo-4,5-dihydro[1,3]thiazolo[4,5-d]pyridazin-2(3H)-ylidene]-2-fluoro-5-(trifluoro methyl)benzamide A mixture of 4-(butylamino)-5-chloro-2-methylpyridazin-3(2H)-one from Example 4A (130 mg, 0.60 mmol) and 2-fluoro-5-(trifluoromethyl)benzoyl isothiocyanate (248 mg, 1 mmol) in dioxane (20 mL) was heated at reflux for 72 hours. The mixture was concentrated under reduced pressure and the residue was dissolved in EtOAc, washed with saturated aqueous NaHCO$_3$ and brine, dried with MgSO$_4$, filtered, and concentrated under reduced pressure. The residue was purified by chromatography (hexanes-EtOAc 3:1) to afford 100 mg of the title compound. MS (ESI) m/z 215 (M+H)$^+$.

Example 4C

N-[(2Z)-3-butyl-5-methyl-4-oxo-4,5-dihydro[1,3]thiazolo[4,5-d]pyridazin-2(3H)-ylidene]-2-{[(2S)-2-hydroxypropyl]oxy}-5-(trifluoromethyl)benzamide Example 4B (240 mg, 0.56 mmol) and (S)-propane-1,2-diol (213 mg, 2.80 mmol) were processed as described in Example 3C to afford the title compound. $^1$H NMR (300 MHz, DMSO-d$_6$) δ ppm 0.94 (t, J=7.46 Hz, 3H) 1.20 (d, J=5.76 Hz, 3H) 1.31-1.45 (m, 2H) 1.72-1.87 (m, 2H) 3.77 (s, 3H) 3.91-4.10 (m, 3H) 4.74-4.90 (m, 3H) 7.37 (d, J=8.48 Hz, 1H) 7.84 (dd, J=8.65, 2.20 Hz, 1H) 8.27 (d, J=2.37 Hz, 1H) 8.52 (s, 1H). MS (ESI) m/z 485 (M+H)$^+$.

Example 5

N-[(2Z)-3-butyl-6-methyl-7-oxo-6,7-dihydro[1,3]thiazolo[4,5-d]pyridazin-2(3H)-ylidene]-2-{[(2S)-2-hydroxypropyl]oxy}-5-(trifluoromethyl)benzamide Example 5A N-[(2Z)-3-butyl-6-methyl-7-oxo-6,7-dihydro[1,3]thiazolo[4,5-d]pyridazin-2(3H)-ylidene]-2-fluoro-5-(trifluoromethyl)benzamide A mixture of 5-(butylamino)-4-chloro-2-methylpyridazin-3(2H)-one from Example 4A (250 mg, 1.16 mmol) and 2-fluoro-5-(trifluoromethyl)benzoyl isothiocyanate (375 mg, 1.51 mmol) in dioxane (20 mL) was heated at 70° C. for 12 hours and at 100° C. for 6 hours. The mixture was concentrated under reduced pressure and the residue was dissolved in EtOAc, washed with saturated aqueous NaHCO$_3$ and brine, dried with MgSO$_4$, filtered, and concentrated under reduced pressure. The residue was purified by chromatography (CH$_2$Cl$_2$-Et$_2$O 19:1)) to afford 110 mg of the title compound. MS (ESI) m/z 429 (M+H)$^+$.

Example 5B

N-[(2Z)-3-butyl-6-methyl-7-oxo-6,7-dihydro[1,3]thiazolo[4,5-d]pyridazin-2(3H)-ylidene]-2-{[(2S)-2-hydroxypropyl]oxy}-5-(trifluoromethyl)benzamide Example 5A (115 mg, 0.27 mmol) and (S)-propane-1,2-diol (102 mg, 1.34 mmol) were processed as described in Example 3C to afford the title compound. $^1$H NMR (300 MHz, DMSO-d$_6$) δ ppm 0.93 (t, J=7.34 Hz, 3H) 1.16-1.25 (m, 3H) 1.32-1.47 (m, 2H) 1.73-1.86 (m, 2H) 3.78 (s, 3H) 3.91-4.09 (m, 3H) 4.47 (t, J=7.34 Hz, 2H) 4.87 (d, J=3.97 Hz, 1H) 7.38 (d, J=8.73 Hz, 1H) 7.85 (dd, J=8.72, 2.38 Hz, 1H) 8.26 (d, J=2.38 Hz, 1H) 8.70 (s, 1H). MS (ESI) m/z 486 (M+H)$^+$.

Example 6

N-[(2Z)-1-butyl[1,3]thiazolo[5,4-d]pyrimidin-2(1H)-ylidene]-6-chloro-4-(trifluoromethyl)pyridine-3-carboxamide A mixture of 1-butylthiazolo[5,4-d]pyrimidin-2(1H)-imine (isolated as a side product of reaction in Example 3C) (84 mg, 0.4 mmol), 6-chloro-4-(trifluoromethyl)nicotinic acid (109 mg, 0.48 mmol) and TBTU (129 mg, 0.4 mmol) in CH$_2$Cl$_2$ (15 mL) was treated with DIEA (0.11 mL, 0.61 mmol) and the resulting mixture was stirred at room temperature for 8 hours. The mixture was washed with saturated aqueous NaHCO$_3$ and brine, dried with MgSO$_4$, filtered, and concentrated under reduced pressure. The residue was purified by chromatography (hexanes-EtOAc 1:1) to afford 120 mg of the title compound. $^1$H NMR (300 MHz, DMSO-d$_6$) δ ppm 0.92 (t, J=7.29 Hz, 3H) 1.35-1.47 (m, 2H) 1.75-1.87 (m, 2H) 4.54 (t, J=7.29 Hz, 2H) 8.10 (s, 1H) 9.13 (s, 1H) 9.20 (s, 1H) 9.27 (s, 1H). MS (ESI) m/z 416 (M+H)$^+$.

Example 7

N-[(2Z)-3-butyl[1,3]thiazolo[4,5-b]pyrazin-2(3H)-ylidene]-6-chloro-4-(trifluoromethyl)pyridine-3-carboxamide 3-butylthiazolo[4,5-b]pyrazin-2(3H)-imine (isolated as a side product from the reaction in Example 2C) (165 mg, 0.79 mmol), 6-chloro-4-(trifluoromethyl)nicotinic acid (214 mg (0.95 mmol), TBTU (254 mg, 0.79 mmol) and DIEA (154 mg, 1.19 mmol) in CH$_2$Cl$_2$ (15 mL) were stirred at room temperature for 12 hours. The mixture was washed with saturated aqueous NaHCO$_3$, brine, dried with MgSO$_4$, filtered, and concentrated under reduced pressure. The residue was purified by chromatography (hexanes-EtOAc 1:1) to afford 120 mg of the title compound. $^1$H NMR (300 MHz, DMSO-d$_6$) δ ppm 0.92 (t, J=7.29 Hz, 3H) 1.31-1.45 (m, 2H) 1.84 (t, J=7.46 Hz, 2H) 4.45-4.54 (m, 2H) 8.11 (s, 1H) 8.60-8.68 (m, 2H) 9.21 (s, 1H). MS (ESI) m/z 416 (M+H)$^+$.

Example 8

N-[(2Z)-3-butyl-5-methyl-4-oxo-4,5-dihydro[1,3]thiazolo[4,5-d]pyridazin-2(3H)-ylidene]-2-(2-hydroxy-2-methylpropoxy)-5-(trifluoromethyl)benzamide Example 4B (30 mg, 0.07 mmol) and 2-methylpropane-1,2-diol (12.62 mg, 0.14 mmol) were processed as described in Example 3C to afford the title compound. $^1$H NMR (300 MHz, DMSO-d$_6$) δ ppm 0.94 (t, J=7.46 Hz, 3H) 1.25 (s, 6H) 1.35-1.45 (m, 2H) 1.76-1.86 (m, 2H) 3.77 (s, 3H) 3.90 (s, 2H) 4.65 (s, 1H) 4.77-4.86 (m, 2H) 7.34 (d, J=8.81 Hz, 1H) 7.84 (dd, J=8.81, 2.37 Hz, 1H) 8.32 (d, J=2.37 Hz, 1H) 8.52 (s, 1H). MS (ESI) m/z 499 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:

1. A compound of formula (I),

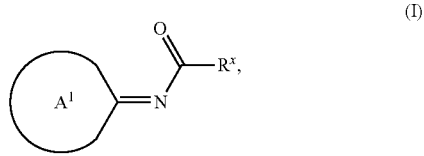

(I)

or a pharmaceutically acceptable salt, solvate, or salt of a solvate thereof, wherein $R^x$ is a phenyl or heteroaryl, each of which is substituted with 2 substituents independently selected from the group consisting of halogen, haloalkyl, —OR$^a$, —OC(O)R$^e$, —C(O)R$^f$, —C(O)OR$^f$, —(CR$^{1a}$R$^{1b}$)$_{q1}$—, —OR$^a$, —(CR$^{1a}$R$^{1b}$)$_{q1}$—OC(O)R$^e$, —(CR$^{1a}$R$^{1b}$)$_{q1}$—C(O)C)R$^f$, and —(CR$^{1a}$R$^{1b}$)$_{q1}$—C(O)OR$^f$;

R$^a$ is —(CR$^{1c}$R$^{1d}$)$_{q2}$—C(O)R$^b$, —(CR$^{1c}$R$^{1d}$)$_{q4}$—OR$^b$, or —(CR$^{1c}$R$^{1d}$)$_{q2}$—OC(O)R$^b$;

R$^b$ and R$^f$, at each occurrence, are each independently hydrogen, alkyl, haloalkyl, G$^b$, hydroxyalkyl, alkoxyalkyl, haloalkoxyalkyl, or —(C$_1$-C$_6$alkylene)-G$^a$;

R$^e$, at each occurrence, is independently alkyl, haloalkyl, G, hydroxyalkyl, alkoxyalkyl, haloalkoxyalkyl, or —(C$_1$-C$_6$ alkylene)-G$^a$;

G$^a$ at each occurrence, is independently aryl, heteroaryl, cycloalkyl, cycloalkenyl, or heterocycle, each of which is independently unsubstituted or substituted with 1, 2, 3, or 4 substituents selected from the group consisting of C$_1$-C$_4$ alkyl, C$_2$-C$_4$ alkenyl, C$_2$-C$_4$alkynyl, halogen, C$_1$-C$_4$ haloalkyl, G$^b$, oxo, —CN, NO$_2$, —OR$^g$, —OC(O)R$^g$, —OC(O)N(R$^g$)$_2$, —S(O)$_2$R$^b$, —S(O)$_2$N(R$^g$)$_2$, —C(O)R$^g$, —C(CO)OR$^g$, —C(O)N(R$^g$)$_2$, —N(R$^g$)$_2$, —N(R$^g$)C(O)R$^g$, —N(R$^f$)S(O)$_2$R$^b$, —N(R$^g$)C(O)O(R$^g$), —N(R$^g$)C(O)N(R$^g$)$_2$, —(CR$^{1e}$R$^{1f}$)$_{q3}$-G$^b$, —(CR$^{1e}$R$^{1f}$)$_{g3}$—OR$^g$, —(CR$^{1e}$R$^{1f}$)$_{q3}$—OC(O)R$^g$, —(CR$^{1e}$R$^f$)$_{g3}$—OC(O)N(R$^g$)$_2$, —(CR$^{1e}$R$^{1f}$)$_{q3}$—S(O)$_2$R$^h$, —(CR$^{1e}$R$^{1f}$)$_{q3}$—S(O)$_2$N(R$^g$)$_2$, —(CR$^{1e}$R$^{1f}$)$_{q3}$—C(O)R$^g$, —(CR$^{1e}$R$^{1f}$)$_{q3}$—C(O)OR$^g$, —(CR$^{1e}$R$^{1f}$)$_{q3}$—C(O)N(R$^g$)$_2$—(CR$^{1e}$R$^{1f}$)$_{q3}$—N(R$^g$)$_2$, —(CR$^{1e}$R$^{1f}$)$_{q3}$—N(R$^g$)C(O)R$^g$, —CR$^{1e}$R$^{1f}$)$_{q3}$—N(R$^g$)S(O)$_2$R$^h$, —(CR$^{1e}$R$^{1f}$)$_{q3}$—N(R$^g$)C(O)O(R$^g$), —(CR$^{1e}$R$^{1f}$)$_{q3}$N(R$^g$)C(O)N(R$^g$)$_2$, and —(CR$^{1e}$R$^{1f}$)$_{q3}$—CN;

G$^b$, at each occurrence, is independently aryl, heteroaryl, cycloalkyl, cycloalkenyl, or heterocycle, each of which is independently unsubstituted or substituted with 1, 2, 3, or 4 substituents selected from the group consisting of —C$_1$-C$_4$ alkyl, C$_2$-C$_4$ alkenyl, C$_2$-C$_4$ alkynyl, halogen, C$_1$-C$_4$ haloalkyl, —CN, NO$_2$, —OR$^j$, —OC(O)R$^j$, —OC(O)N(R$^j$)$_2$, —S(O)$_2$R$^k$, —S(O)$_2$N(R$^j$)$_2$, —C(O)R$^j$, C(O)OR$^j$, —C(O)N(R$^j$)$_2$, —N(R$^j$)$_2$, —N(R$^j$)C(O)R$^j$, N(R$^j$)S(O)$_2$R$^j$, N(R$^j$)C(O)O(R$^j$), —N(R$^j$)C(O)N(R$^j$)$_2$, —(CR$^{1e}$R$^{1f}$)$_{q3}$—OR$^j$, —(CR$^{1e}$R$^{1f}$)$_{q3}$—OC(O)R$^j$, —(CR$^{1e}$R$^{1f}$)$_{q3}$—OC(O)N(R$^j$)$_2$, —(CR$^{1e}$R$^{1f}$)$_{q3}$—S(O)$_2$R$^k$, —(CR$^{1e}$R$^{1f}$)$_{q3}$—S(O)$_2$N(R$^j$)$_2$, —(CR$^{1e}$R$^{1f}$)$_{q3}$—C(O)R$^j$, —(CR$^{1e}$R$^{1f}$)$_{q3}$—C(O)OR$^j$, —(CR$^{1e}$R$^{1f}$)$_{q3}$—C(O)N(R$^j$)$_2$, —(CR$^{1e}$R$^{1f}$)$_{q3}$—N(R$^j$)$_2$, —(CR$^{1e}$R$^{1f}$)$_{q3}$—N(R$^j$)C(O)R$^j$, —(CR$^{1e}$R$^{1f}$)$_{q3}$—N(R$^j$)S(O)$_2$R$^k$, —(CR$^{1e}$R$_{1f}$)$_{q3}$—N(R$^j$)C(O)O(R$^j$), —CR$^{1e}$R$^{1f}$)$_{q3}$—N(R$^j$)C(O)N(R$^j$)$_2$, and —(CR$^{1e}$R$^{1f}$)$_{q3}$—CN;

R$^{1a}$, R$^{1b}$, R$^{1c}$, R$^{1d}$, R$^{1e}$, and R$^{1f}$, at each occurrence, are each independently hydrogen, halogen, alkyl,, or haloalkyl;

R$^g$, at each occurrence, is independently hydrogen, alkyl, haloalkyl, G$^b$, hydroxyalkyl, alkoxyalkyl, haloalkoxyl, or —(C$_1$-C$_6$ alkylene)-G$^b$;

R$^h$, at each occurrence, is independently alkyl, haloalkyl, G$^b$, hydroxyalkyl, alkoxyalkl, haloalkoxy, or —(C$_1$-C$_6$ alkylene)-G$^b$;

R$^j$, at each occurrence, is independently hydrogen, alkyl, or haloalkyl;

R$^k$, at each occurrence, is independently alkyl or haloalkyl;

A$^1$ is formula (a):

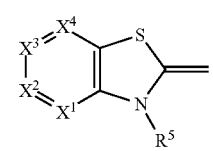

(a)

X$^1$ is CR$^1$;

X$^2$ is N;

X$^3$ is CR$^3$;

X$^4$ is N;

R$^1$ and R$^3$ can be the same or different, are each independently hydrogen, hydroxy, alkoxy, haloalkoxy, halogen, alkyl, or haloalkyl;

R$^5$, at each occurrence, is the same or different, and is independently C$_2$-C$_{10}$ alkyl, alkenyl, alkynyl, or haloalkyl;

q1, q2, and q3, at each occurrence, are each independently 1, 2, 3, 4, or 5; and q4, at each occurrence, is independently 2, 3, 4, or 5.

2. The compound according to claim 1 or a pharmaceutically acceptable salt, solvate, or salt of a solvate thereof, wherein R$^x$ is phenyl and R$^5$ is C$_2$-C$_{10}$alkyl.

3. The compound according to claim 1 or a pharmaceutically acceptable salt, solvate, or salt of a solvate thereof, wherein R$^x$ is heteroaryl and R$^5$ is C$_2$-C$_{10}$ alkyl.

4. The compound according to claim 1 or a pharmaceutically acceptable salt, solvate, or salt of a solvate thereof wherein R$^5$ is C$_2$-C$_{10}$ alkyl or haloalkyl.

5. The compound according to claim 1 or a pharmaceutically acceptable salt, solvate, or salt of a solvate thereof, wherein R$^x$ is a phenyl or a heteroaryl wherein the heteroaryl is pyridinyl.

6. The compound according to claim 1 selected from the group consisting of
- N-[(2Z)-1-butyl-7-hydroxy[1,3]thiazolo[5,4-d]pyrimidin-2(1H)-ylidene]-2-{[(S)-2-hyodroxypropyl]oxy}-5-(trifluoromethyl)benzamide;
- N-[(2Z)-1-butyl[1,3]thiazolo[5,4-d]pyrimidin-2(1H)-ylidene]-2-{[(2S)-2-hydroxypropy]oxy}-5-(trifluoromethyl)benzamide; and
- N-[(2Z)-1-butyl[1,3]thizolo[5,4-d]pyrimidin-2(1H)-ylidene]-6-chloro-4-(trifluoromethyl)pyridine-3-carboxamide;

a pharmaceutically acceptable salt, solvate, or salt of a solvate thereof.

7. A pharmaceutical composition comprising a therapeutically effective amount of a compound of formula (I) according to claim 1 or a pharmaceutically acceptable salt, solvate, or salt of a solvate thereof; in combination with a pharmaceutically acceptable carrier.

8. A method for treating pain in a mammal in need of such treatment comprising administering to the mammal a therapeutically effective amount of a compound of formula (I) according to claim 1, or a pharmaceutically acceptable salt, solvate, or salt of a solvate thereof.

* * * * *